United States Patent
Boyden et al.

(10) Patent No.: US 10,330,674 B2
(45) Date of Patent: Jun. 25, 2019

(54) PUMILIO DOMAIN-BASED MODULAR PROTEIN ARCHITECTURE FOR RNA BINDING

(71) Applicant: Massachusetts Institute of Technology, Cambridge, MA (US)

(72) Inventors: Edward S. Boyden, Chestnut Hill, MA (US); Katarzyna P. Adamala, Somerville, MA (US); Daniel Alberto Martin-Alarcon, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/995,169

(22) Filed: Jan. 13, 2016

(65) Prior Publication Data

US 2016/0238593 A1 Aug. 18, 2016

Related U.S. Application Data

(60) Provisional application No. 62/103,014, filed on Jan. 13, 2015.

(51) Int. Cl.
*C40B 40/10* (2006.01)
*G01N 33/53* (2006.01)
*C07K 14/47* (2006.01)

(52) U.S. Cl.
CPC ......... *G01N 33/5308* (2013.01); *C07K 14/47* (2013.01); *C40B 40/10* (2013.01)

(58) Field of Classification Search
None
See application file for complete search history.

(56) References Cited

U.S. PATENT DOCUMENTS 9,499,805 B2 11/2016 Wang
9,580,714 B2 2/2017 Filipovska

FOREIGN PATENT DOCUMENTS

WO WO2010/0075303 A1 7/2010

OTHER PUBLICATIONS

Lionnet et al. (2011) Nature Methods vol. 8 pp. 165 to 170.*

(Continued)

*Primary Examiner* — Christian C Boesen
(74) *Attorney, Agent, or Firm* — Norma E. Henderson

(57) ABSTRACT

A programmable modular protein architecture for RNA binding comprises a set of modules, derived from RNA-binding protein Pumilio, that can be concatenated into chains of varying composition and length. When bound into a chain, each module has a preferred affinity for a specific RNA base. The chains can bind arbitrary RNA sequences with high specificity and fidelity by varying the sequence of modules within the chains. Each module contains at least 6 amino acids, with the amino acids in positions 1 and 5 providing the preferred affinity for the specific base, and the amino acid at position 2 serving as a stacking unit between concatenated modules. The modules may have four canonic forms, each having a preferred affinity for a different base and characterized by the base with which it has affinity, the two amino acids that provide the affinity, and the amino acid that serves as a stacking unit.

21 Claims, 27 Drawing Sheets

Specification includes a Sequence Listing.

(56) References Cited

OTHER PUBLICATIONS

Chen, Yu, et al., Finding the Missing Code of RNA Recognition by PUF Proteins, Jul. 29, 2011, Chemistry & Biology 18, pp. 821-823.

Choudhury, Rajarshi et al., Engineering RNA Endonucleases with Customized Sequence Specificities, 2012, Nat. Commun. 3:1147.

Dong, Shuyun, et al., Specific and Modular Binding Code for Cytosine Recognition in Pumilio/FBF (PUF) RNA-binding Domains, Jun. 8, 2011, The Journal of biological chemistry 286, pp. 26732-26742.

Abil, Zhanar, et al., Modular assembly of designer PUF proteins for specific post-transcriptional regulation of endogenous RNA, 2014, J Biol Eng 8(1):7.

Cao, Jicong, et al., Bidirectional regulation of mRNA translation in mammalian cells by using PUF domains, 2014, Angew Chemie—Int Ed 53(19):4900-4904.

Cheong, Cheom-Gil, et al., Engineering RNA sequence specificity of Pumilio repeats, 2006, Proc Natl Acad Sci U S A 103(37):13635-13639.

Filipovska, Aleksandra, et al., A universal code for RNA recognition by PUF proteins, 2011, Nat Chem Biol 7 (7)425-427.

Ozawa, Takeaki, et al., Imaging dynamics of endogenous mitochondrial RNA in single living cells, 2007, Nat Methods 4(5):413-419.

Tilsner, Jens, et al., Live-cell imaging of viral RNA genomes using a Pumilio-based reporter, 2009, Plant J 57(4):758-770.

Wang, Yang, et al., Engineering splicing factors with designed specificities, 2009, Nat Methods 6(11):825-30.

Yamada, Toshimichi, et al., Visualization of nonengineered single mRNAs in living cells using genetically encoded fluorescent probes, 2011, Anal Chem 83(14):5708-5714.

Yoshimura, Hideaki, et al., Fluorescent probes for imaging endogenous beta-actin mRNA in living cells using fluorescent protein-tagged pumilio, 2012 ACS Chem Biol 7(6):999-1005.

* cited by examiner

| PumHD UNIT | AA1 | AA2 | AA5 | BASE |
|---|---|---|---|---|
| 1 | S | R | Q | A |
|   | N | R | Q | U |
|   | S | R | E | G |
|   | S | R | R | C |
| 2 | C | Y | Q | A |
|   | N | Y | Q | U |
|   | S | Y | E | G |
|   | S | Y | R | C |
| 3 | C | R | Q | A |
|   | N | R | Q | U |
|   | S | R | E | G |
|   | S | R | R | C |
| 4 | C | Y | Q | A |
|   | N | Y | Q | U |
|   | S | Y | E | G |
|   | S | Y | R | C |
| 5 | C | R | Q | A |
|   | N | R | Q | U |
|   | S | R | E | G |
|   | S | R | R | C |
| 6 | C | Y | Q | A |
|   | N | Y | Q | U |
|   | S | Y | E | G |
|   | S | Y | R | C |
| 7 | C | N | Q | A |
|   | N | N | Q | U |
|   | S | N | E | G |
|   | S | Y | R | C |
| 8 | C | Y | Q | A |
|   | N | Y | Q | U |
|   | S | Y | E | G |
|   | S | Y | R | C |

FIG. 3

SEQUENCE LISTING

```
<160> NUMBER OF SEQ ID NOS: 26

<210> SEQ ID NO 1
<211> LENGTH: 10
<212> TYPE: RNA
<213> ORGANISM: Unknown
<220> FEATURE:
<223> OTHER INFORMATION: target for variable length Pumby sequence

<400> SEQUENCE: 1
auauauguaa                                                          10

<210> SEQ ID NO 2
<211> LENGTH: 11
<212> TYPE: RNA
<213> ORGANISM: Unknown
<220> FEATURE:
<223> OTHER INFORMATION: target for variable length Pumby sequence

<400> SEQUENCE: 2
auauauguaa g                                                        11

<210> SEQ ID NO 3
<211> LENGTH: 12
<212> TYPE: RNA
<213> ORGANISM: Unknown
<220> FEATURE:
<223> OTHER INFORMATION: target for variable length Pumby sequence

<400> SEQUENCE: 3
auauauguaa gg                                                       12

<210> SEQ ID NO 4
<211> LENGTH: 13
<212> TYPE: RNA
<213> ORGANISM: Unknown
<220> FEATURE:
<223> OTHER INFORMATION: target for variable length Pumby sequence

<400> SEQUENCE: 4
auauauguaa ggc                                                      13

<210> SEQ ID NO 5
<211> LENGTH: 14
<212> TYPE: RNA
<213> ORGANISM: Unknown
<220> FEATURE:
<223> OTHER INFORMATION: target for variable length Pumby sequence

<400> SEQUENCE: 5
auauauguaa ggcg                                                     14
```

```
<210> SEQ ID NO 6
<211> LENGTH: 15
<212> TYPE: RNA
<213> ORGANISM: Unknown
<220> FEATURE:
<223> OTHER INFORMATION: target for variable length Pumby sequence

<400> SEQUENCE: 6
auauauguaa ggcgg                                                        15

<210> SEQ ID NO 7
<211> LENGTH: 16
<212> TYPE: RNA
<213> ORGANISM: Unknown
<220> FEATURE:
<223> OTHER INFORMATION: target for variable length Pumby sequence

<400> SEQUENCE: 7
auauauguaa ggcggc                                                       16

<210> SEQ ID NO 8
<211> LENGTH: 17
<212> TYPE: RNA
<213> ORGANISM: Unknown
<220> FEATURE:
<223> OTHER INFORMATION: target for variable length Pumby sequence

<400> SEQUENCE: 8
auauauguaa ggcggcu                                                      17

<210> SEQ ID NO 9
<211> LENGTH: 18
<212> TYPE: RNA
<213> ORGANISM: Unknown
<220> FEATURE:
<223> OTHER INFORMATION: target for variable length Pumby sequence

<400> SEQUENCE: 9
auauauguaa ggcggcuu                                                     18

<210> SEQ ID NO 10
<211> LENGTH: 18
<212> TYPE: RNA
<213> ORGANISM: Unknown
<220> FEATURE:
<223> OTHER INFORMATION: target for variable length Pumby sequence

<400> SEQUENCE: 10
uucggcggaa ugaugguu                                                     18

<210> SEQ ID NO 11
<211> LENGTH: 10
<212> TYPE: RNA
<213> ORGANISM: Unknown
<220> FEATURE:
<223> OTHER INFORMATION: target for Pumby 10mer

<400> SEQUENCE: 11
ggggucgccg                                                              10

<210> SEQ ID NO 12
<211> LENGTH: 10
<212> TYPE: RNA
<213> ORGANISM: Unknown
<220> FEATURE:
<223> OTHER INFORMATION: target for Pumby 10mer
```

-continued

```
<400> SEQUENCE: 12
gccgugacua                                                           10

<210> SEQ ID NO 13
<211> LENGTH: 10
<212> TYPE: RNA
<213> ORGANISM: Unknown
<220> FEATURE:
<223> OTHER INFORMATION: target for Pumby 10mer

<400> SEQUENCE: 13
gguaccucua                                                           10

<210> SEQ ID NO 14
<211> LENGTH: 24
<212> TYPE: DNA
<213> ORGANISM: Unknown
<220> FEATURE:
<223> OTHER INFORMATION: Pumby 8mer landing site sequence

<400> SEQUENCE: 14
acacggccac cgucccagcg uguc                                           24

<210> SEQ ID NO 15
<211> LENGTH: 24
<212> TYPE: DNA
<213> ORGANISM: Unknown
<220> FEATURE:
<223> OTHER INFORMATION: PumHD landing site sequence

<400> SEQUENCE: 15
acgaaggcua cgucccagcg uguc                                           24

<210> SEQ ID NO 16
<211> LENGTH: 24
<212> TYPE: DNA
<213> ORGANISM: Unknown
<220> FEATURE:
<223> OTHER INFORMATION: Pumby 8mer landing site sequence

<400> SEQUENCE: 16
acgcccgaca cgucccagcg uguc                                           24

<210> SEQ ID NO 17
<211> LENGTH: 24
<212> TYPE: DNA
<213> ORGANISM: Unknown
<220> FEATURE:
<223> OTHER INFORMATION: Pumby 8mer landing site sequence

<400> SEQUENCE: 17
accugcugug cgucccagcg uguc                                           24

<210> SEQ ID NO 18
<211> LENGTH: 24
<212> TYPE: DNA
<213> ORGANISM: Unknown
<220> FEATURE:
<223> OTHER INFORMATION: Pumby 8mer landing site sequence

<400> SEQUENCE: 18
acgagcgaca cgucccagcg uguc                                           24

<210> SEQ ID NO 19
<211> LENGTH: 24
```

```
<212> TYPE: DNA
<213> ORGANISM: Unknown
<220> FEATURE:
<223> OTHER INFORMATION: PumHD landing site sequence

<400> SEQUENCE: 19
acgacaacag cgucccagcg uguc                                          24

<210> SEQ ID NO 20
<211> LENGTH: 24
<212> TYPE: DNA
<213> ORGANISM: Unknown
<220> FEATURE:
<223> OTHER INFORMATION: Pumby 8mer landing site sequence

<400> SEQUENCE: 20
acgacagatt cgucccagcg uguc                                          24

<210> SEQ ID NO 21
<211> LENGTH: 19
<212> TYPE: DNA
<213> ORGANISM: Unknown
<220> FEATURE:
<223> OTHER INFORMATION: Golden Gate starting material (Fig. 39)

<400> SEQUENCE: 21
gtcaggtctc acagtatag                                                19

<210> SEQ ID NO 22
<211> LENGTH: 19
<212> TYPE: DNA
<213> ORGANISM: Unknown
<220> FEATURE:
<223> OTHER INFORMATION: Golden Gate starting material (Fig. 39)

<400> SEQUENCE: 22
cagaccagag tgtcatatc                                                19

<210> SEQ ID NO 23
<211> LENGTH: 19
<212> TYPE: DNA
<213> ORGANISM: Unknown
<220> FEATURE:
<223> OTHER INFORMATION: Golden Gate reconstituted starting material
      (Fig. 39)

<400> SEQUENCE: 23
gtcaggtctc acagtatag                                                19

<210> SEQ ID NO 24
<211> LENGTH: 19
<212> TYPE: DNA
<213> ORGANISM: Unknown
<220> FEATURE:
<223> OTHER INFORMATION: Golden Gate reconsittuted starting material
      (Fig. 39)

<400> SEQUENCE: 24
cagaccagag tgtcatatc                                                19

<210> SEQ ID NO 25
<211> LENGTH: 12
<212> TYPE: DNA
<213> ORGANISM: Unknown
<220> FEATURE:
<223> OTHER INFORMATION: Golden Gate end product (Fig. 39)
```

```
<400> SEQUENCE: 25
agcgcagtat ag                                                          12

<210> SEQ ID NO 26
<211> LENGTH: 12
<212> TYPE: DNA
<213> ORGANISM: Unknown
<220> FEATURE:
<223> OTHER INFORMATION: Golden Gate end product (Fig. 39)

<400> SEQUENCE: 26
tcgcgtcata tc                                                          12
```

PUMILIO DOMAIN-BASED MODULAR PROTEIN ARCHITECTURE FOR RNA BINDING

RELATED APPLICATIONS

This application claims the benefit of U.S. Provisional Application Ser. No. 62/103,014, filed Jan. 13, 2015, the entire disclosure of which is herein incorporated by reference.

STATEMENT REGARDING FEDERALLY SPONSORED RESEARCH OR DEVELOPMENT

This invention was made with U.S. government support under Grant Numbers R01 NS075421, R01 MH103910, and U01 MH106011, awarded by the National Institutes of Health. The government has certain rights in this invention.

FIELD OF THE TECHNOLOGY

The present invention relates to programmable biology and, in particular, to programmable RNA binding proteins.

BACKGROUND

Many scientific questions and bioengineering goals relate to the monitoring and control of RNA functions in living cells. The ability to monitor and perturb RNA in living cells would benefit greatly from a way of systematically targeting unmodified RNA sequences for observation and control. Proteins that can bind arbitrary DNA sequences in a modular fashion, such that varying the sequence of building blocks in a given protein can result in essentially any DNA sequence being targeted [Buxbaum A R, Haimovich G, Singer R H (2014) In the right place at the right time: visualizing and understanding mRNA localization. Nat Rev Mol Cell Biol 16(2):95-109], are having much impact in the study and engineering of genomes. If a similar protein architecture could be devised for RNA sequences, so that any RNA sequence could be targeted simply by varying the sequence of building blocks within a designed protein, this could open up new abilities for the observation, control, and mapping of endogenous RNAs and their products.

A powerful strategy is to modify a target RNA by inserting an exogenous sequence like MS2 or PP7, so that the corresponding RNA binding protein can deliver a reporter or RNA modification enzyme to an RNA of interest [Bogdanove, A. J. & Voytas, D. F. TAL effectors: customizable proteins for DNA targeting. Science 333, 1843-1846 (2011); Miller, M. T., Higgin, J. J. & Hall, T. M. T. Basis of altered RNA-binding specificity by PUF proteins revealed by crystal structures of yeast Puf4p. Nature structural & molecular biology 15, 397-402 (2008); Wang, X., Zamore, P. D. & Hall, T. M. Crystal structure of a Pumilio homology domain. Mol Cell 7, 855-865 (2001)]. Ideally one could target unmodified RNA, both for simplicity and to preserve as much native RNA structure and function as possible [Re A, Joshi T, Kulberkyte E, Morris Q, Workman C T (2014) RNA-protein interactions: an overview. Methods Mol Biol 1097:491-521; Chen Y, Varani G (2013) Engineering RNA-binding proteins for biology. FEBS J 280(16):3734-3754]. It has been proposed that proteins such as the C. elegans Puf [Campbell Z T, Valley C T, Wickens M (2014) A protein-RNA specificity code enables targeted activation of an endogenous human transcript. Nat Struct Mol Biol 21(8): 732-738], the human PumHD [Abil Z, Denard C A, Zhao H (2014) Modular assembly of designer PUF proteins for specific post-transcriptional regulation of endogenous RNA. J Biol Eng 8(1):7], or members of the pentatricopeptide family [Coquille S, et al. (2014) An artificial PPR scaffold for programmable RNA recognition. Nat Commun 5:5729] could serve such a purpose. Each of these proteins is made of many similar units, each of which binds one RNA base.

The most extensively studied protein architecture, in the context of prospective universal single stranded RNA targeting in mammalian cells, is the human Pumilio homology domain (PumHD) [Filipovska A, Rackham 0 (2012) Modular recognition of nucleic acids by PUF, TALE and PPR proteins. Mol Biosyst 8(3):699-708; Moore F L, et al. (2003) Human Pumilio-2 is expressed in embryonic stem cells and germ cells and interacts with DAZ (Deleted in AZoospermia) and DAZ-like proteins. Proc Natl Acad Sci USA 100(2):538-43; Lunde B M, Moore C, Varani G (2007) RNA-binding proteins: modular design for efficient function. Nat Rev Mol Cell Biol 8(6):479-90; Wickens M, Bernstein D S, Kimble J, Parker R (2002) A PUF family portrait: 3'UTR regulation as a way of life. Trends Genet 18(3):150-157]. PumHD is a protein of 10 units, of which 8 units bind to the bases of an 8-nucleobase target RNA sequence, called the Nanos Response Element (NRE), in the reverse orientation 3' AUAUAUGU 5' [Spassov D S, Jurecic R (2002) Cloning and comparative sequence analysis of PUM1 and PUM2 genes, human members of the Pumilio family of RNA-binding proteins. Gene 299(1-2):195-204; Wang X, Zamore P D, Hall T M T, Tanaka Hall T M (2001) Crystal structure of a Pumilio homology domain. Mol Cell 7(4):855-865; Wang X, McLachlan J, Zamore P D, Hall T M T (2002) Modular Recognition of RNA by a Human Pumilio-Homology Domain. Cell 110(4):501-512; Cheong C-G, Hall T M T (2006) Engineering RNA sequence specificity of Pumilio repeats. Proc Natl Acad Sci USA 103(37): 13635-13639; Zamore P D, Williamson J R, Lehmann R (1997) The Pumilio protein binds RNA through a conserved domain that defines a new class of RNA-binding proteins. RNA 3(12):1421-33; Miller M T, Higgin J J, Tanaka Hall T M, Hall T M T (2008) Basis of altered RNA-binding specificity by PUF proteins revealed by crystal structures of yeast Puf4p. Nat Struct Mol Biol 15(4):397-402; Qiu C, et al. (2012) Divergence of Pumilio/fem-3 mRNA binding factor (PUF) protein specificity through variations in an RNA-binding pocket. J Biol Chem 287(9):6949-57]. X-ray structures of the PumHD-NRE complex indicate that three key amino acids interact with each RNA nucleobase [Wang X, Zamore P D, Hall T M T, Tanaka Hall T M (2001) Crystal structure of a Pumilio homology domain. Mol Cell 7(4): 855-865; Chen Y, Varani G (2011) Finding the missing code of RNA recognition by PUF proteins. Chem Biol 18(7):821-3].

A number of pioneering studies have shown that modifications of the wild-type PumHD can indeed bind to many sequences other than the NRE, strongly pointing towards the modularity of PumHD (the shorthand 'Pum' is used herein to denote any protein homologous to or derived from PumHD). Given the rich set of previous findings related to Pum proteins, it would be useful to devise a set of four canonical protein modules, each of which targets one RNA base with high specificity and fidelity, and which could be concatenated in chains of varying composition and length so as to bind desired target RNAs. A similar protein architecture, the TAL effector, has been rendered in this single-module form and has proven to be useful for targeting DNA because of its modularity [Miller J C, et al. (2011) A TALE nuclease architecture for efficient genome editing. Nat Biotechnol 29(2):143-8; Sander J D, et al. (2011) Targeted gene disruption in somatic zebrafish cells using engineered TAL-ENs. Nat Biotechnol 29(8):697-8]). There are four canonical TALE protein modules, each of which targets one DNA base with high specificity and fidelity. If analogous Pum modules could be developed, they could be easily designed and used: simply concatenate a chain of modules according to the sequence of a natural target RNA, and then the protein (perhaps equipped with various reporters and effectors) could be targeted to a desired RNA.

Previous works have demonstrated, using proteins that bind to specific RNA sequences, the measurement of mRNA expression level [Ozawa T, Natori Y, Sato M, Umezawa Y (2007) Imaging dynamics of endogenous mitochondrial RNA in single living cells. Nat Methods 4(5):413-419; Yamada T, Yoshimura H, Inaguma A, Ozawa T (2011) Visualization of nonengineered single mRNAs in living cells using genetically encoded fluorescent probes. Anal Chem 83(14):5708-5714], imaging of mRNA dynamics [Ozawa T, Natori Y, Sato M, Umezawa Y (2007) Imaging dynamics of endogenous mitochondrial RNA in single living cells. Nat Methods 4(5):413-419. Yamada T, Yoshimura H, Inaguma A, Ozawa T (2011) Visualization of nonengineered single mRNAs in living cells using genetically encoded fluorescent probes. Anal Chem 83(14):5708-5714; Yoshimura H, Inaguma A, Yamada T, Ozawa T (2012) Fluorescent probes for imaging endogenous β-actin mRNA in living cells using fluorescent protein-tagged pumilio. ACS Chem Biol 7(6): 999-1005; Tilsner J, et al. (2009) Live-cell imaging of viral RNA genomes using a Pumilio-based reporter. Plant J 57(4): 758-770; Tilsner J (2015) Pumilio-based RNA in vivo imaging. Methods Mol Biol 1217:295-328], and enhancement and suppression of mRNA translation [Campbell Z T, Valley C T, Wickens M (2014) A protein-RNA specificity code enables targeted activation of an endogenous human transcript. Nat Struct Mol Biol 21(8):732-738; Cao J, et al. (2013) Light-inducible activation of target mRNA translation in mammalian cells. Chem Commun (Camb) 49(75): 8338-40; Cao J, Arha M, Sudrik C, Schaffer D V., Kane R S (2014) Bidirectional regulation of mRNA translation in mammalian cells by using PUF domains. Angew Chemie—Int Ed 53(19):4900-4904; Choudhury R, Tsai Y S, Dominguez D, Wang Y, Wang Z (2012) Engineering RNA endonucleases with customized sequence specificities. Nat Commun 3:1147].

SUMMARY

In one aspect, the invention is a modular protein architecture for RNA binding. In another aspect, the invention is a universal programmable RNA-binding protein based on the Pumilio domain architecture and composed of repeats of a single modular unit. The RNA-binding protein PumHD (Pumilio Homology Domain) yields a set of four canonical protein modules, each of which binds to one RNA base with high specificity and fidelity. These modules can be concatenated in chains of varying composition and length, thereby providing the ability to bind essentially arbitrary RNA sequences, a novel architecture that is referred to throughout this disclosure as "Pumilio-based assembly" or "Pumby". Pumby implementations show utility in a wide variety of contexts, including, but not limited to, programmable scaffolding of proteins, quantifying RNA translation, and suppressing and enhancing the translation of specific RNAs. The Pumby architecture may further prove useful for many applications in the imaging, measurement, manipulation, and biotechnological utilization of specific endogenous RNA targets in intact cells and systems.

The single-stranded RNA-binding protein PumHD has been widely used in native and modified form to target different RNAs for monitoring and perturbation. To enable easy design of RNA binding proteins capable of targeting RNAs of varying length, a set of four modular protein building blocks were developed, each of which targets one RNA base with high specificity and fidelity. These blocks can be concatenated in chains of varying composition and length, so as to bind single-stranded target RNAs. The use of these modules was validated in a variety of traditional targeted-RNA degradation and translation initiation settings. The architecture can perform RNA-directed protein assembly and enhancement of translation of unmodified RNAs, and further demonstrates a new use of such proteins, measurement and monitoring of RNA translation in living cells.

In various aspects, the invention includes the design and cloning scheme of PumHD variants for arbitrary specificity, the design and cloning scheme of Pumby, which includes several variants that use different units of PumHD as the universal binding unit, as well as different stacking amino acids between them, and the use of PumHD and Pumby for scaffolding proteins into RNA-programmable assemblies. Further included are all of the Pumby variants, being any number of PumHD units (thus binding to any size of RNA target) assembled using any single unit of WT Pum repeated given number of times, with amino acids Tyrosine or Arginine as stacking amino acids on position 2.

In one aspect of the invention, a modular protein architecture for RNA binding comprises a set of protein modules derived from the RNA-binding protein Pumilio. The protein modules can be concatenated into chains of varying composition and length. Each protein module, when bound into a chain, has a preferred affinity for a specific target RNA base. The concatenated chains of protein modules provide the ability to bind arbitrary RNA sequences with high specificity and fidelity by varying the sequence of the protein modules within the chains. Each protein module contains at least 6 amino acids selected such that the amino acids in positions 1 and 5 provide the preferred affinity of the protein module for the specific RNA base, and the amino acid at position 2 serves as a stacking unit between concatenated modules.

In some embodiments, the protein modules have four canonic forms, with each canonic form having a preferred affinity for a different RNA base. The four canonic forms may be characterized by the RNA base with which they have a preferred affinity, the two amino acids of the protein module that provide the preferred affinity for that base, and the amino acid of the protein module that serves as a stacking unit between concatenated protein modules. In a preferred embodiment, the four canonic forms include Form 1, which has a preferred affinity for RNA base Adenine, and has Cysteine at position 1, Tyrosine at position 2, and Glutamine at position 5; Form 2, which has a preferred affinity for RNA base Uracil, and has Asparagine at position 1, Tyrosine at position 2, and Glutamine at position 5; Form 3, which has a preferred affinity for RNA base Guanine, and has Serine at position 1, Tyrosine at position 2, and Glutamic Acid at position 5; and Form 4, which has a preferred affinity for RNA base Cytosine, and has Serine at position 1, Tyrosine at position 2, and Arginine at position 5. In some embodiments, the protein modules are 8-mers derived from the Pumilio Homology Domain. In some embodiments, the stacking unit at position 2 is Tyrosine or Arginine.

In another aspect of the invention, a universal programmable RNA-binding protein is derived from the RNA-binding protein Pumilio and comprises a modular unit that can be concatenated with other modular units. When concatenated with other modular units, the modular unit has a preferred affinity for a specific RNA base with high specificity and fidelity. A modular unit contains at least 6 amino acids selected so that the amino acids in positions 1 and 5 provide the preferred affinity of the modular unit for the specific RNA base, and the amino acid at position 2 is configurable to serve as a stacking unit between concatenated modular units.

In some embodiments, the modular unit has a preferred affinity for RNA base Adenine, modular unit amino acid 1 is Cysteine, modular unit amino acid 2 is Tyrosine, and modular unit amino acid 5 is Glutamine. In some embodiments, the modular unit has a preferred affinity for RNA base Uracil, modular unit amino acid 1 is Asparagine, modular unit amino acid 2 is Tyrosine, and modular unit amino acid 5 is Glutamine. In some embodiments, the modular unit has a preferred affinity for RNA base Guanine, modular unit amino acid 1 is Serine, modular unit amino acid 2 is Tyrosine, and modular unit amino acid 5 is Glutamic Acid. In some embodiments, the modular unit has a preferred affinity for RNA base Cytosine, modular unit amino acid 1 is Serine, modular unit amino acid 2 is Tyrosine, and modular unit amino acid 5 is Arginine. In some embodiments, the modular unit is an 8-mer derived from the Pumilio Homology Domain.

An RNA binding protein assembly architecture according to one aspect of the invention comprises a set of four universal programmable RNA-binding proteins, wherein each RNA-binding protein in the set has a preferred affinity for a different RNA base. The RNA binding protein assembly architecture may comprise a plurality of each of the four universal programmable RNA-binding proteins.

In yet another aspect of the invention, a method for binding an RNA molecule of arbitrary sequence length and composition includes the steps of: producing a set of protein modules derived from the RNA-binding protein Pumilio, wherein each protein module, when concatenated with other protein modules, has a preferred affinity for a specific target RNA base with high specificity and fidelity; concatenating selected ones of the protein modules into a chain of suitable composition and length for binding the RNA molecule; and binding the RNA molecule to the chain of concatenated protein modules.

BRIEF DESCRIPTION OF THE DRAWINGS

Other aspects, advantages and novel features of the invention will become more apparent from the following detailed description of the invention when considered in conjunction with the accompanying drawings, wherein:

FIG. 3 depicts an example literature-derived consensus sequence for how to change PumHD so that any unit may bind any base.

FIGS. 20-27 depict an assay for validating the ability of Pum proteins to report translation levels and the results thereof, wherein:

FIG. 20 is a schematic of the reporter plasmids used;

FIG. 21 depicts the target RNAs, each fused to half of split Firefly luciferase;

FIG. 22 depicts GFP levels measured for extracts of HEK293FT cells transfected with either GFP-BLA or BLA-GFP (as in FIG. 21), as well as both reporter plasmids (as in FIG. 20);

FIG. 23 reports BLA activity from the same set of biological replicates as FIG. 22;

FIG. 24 is a graphical representation of firefly luciferase reconstitution mediated by Pum reassembly on RNA scaffolds, for three Pum binding sites in the GFP sequence, for cells transfected with either GFP-BLA or BLA-GFP (or no target) as well as both reporter plasmids from FIG. 20;

FIG. 25 is a graphical representation of firefly luciferase reconstitution as in FIG. 24, but for Pum binding sites in the BLA sequence;

FIG. 26 graphically depicts RT-qPCR measurement of the GFP transcript for the experiments of FIG. 24; and FIG. 27 graphically depicts RT-qPCR measurement as in FIG. 26, but for the experiments of FIG. 25.

DETAILED DESCRIPTION

Figure 1:
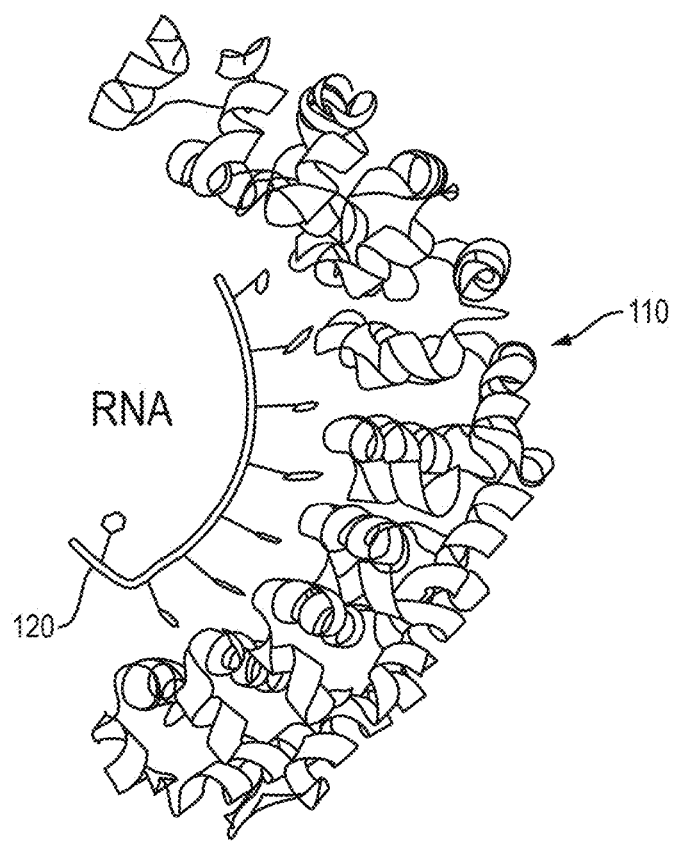
FIG. 1 depicts the crystal structure of the wild-type human Pumilio Homology Domain (PumHD) with its cognate RNA.

In one aspect, the invention is a programmable RNA binding protein composed of repeats of a single modular unit. The RNA-binding protein PumHD (Pumilio Homology Domain) yields a set of four canonical modules, each of which binds to one RNA base with high specificity and fidelity. These modules can be concatenated in chains of varying length, to bind essentially arbitrary RNA sequences, a novel architecture called "Pumilio-based assembly" or "Pumby". The modular protein architecture of one aspect of the invention comprises four protein building blocks derived from the Pumilio protein that enable universal RNA targeting and engineered for concatenation in chains ranging from 6 to 18 modules in length The Pumby implementations show utility in a wide variety of contexts, including programmable scaffolding of proteins, quantifying RNA translation, and suppressing and enhancing the translation of specific RNAs. The Pumby architecture also is useful for many applications in the imaging, manipulation, and biotechnological utilization of specific RNA targets in intact cells and systems.

In one aspect, the invention is a protein technology that enables binding to arbitrary sequences of RNA in living cells. The technology, based on the Pumilio domain architecture, has been developed into two variants called PumHD and Pumby. PumHD is modified version of the WT Pumilio protein that exhibits programmable binding to arbitrary 8-base sequences of RNA. Each of the eight units of PumHD can bind to all four RNA bases, and the RNA bases flanking the target sequence do not affect binding. Pumby is a more simple and modular form of PumHD, in which a single protein unit of PumHD is concatenated into arrays of arbitrary size and binding sequence specificity. Of the many units of PumHD that can be used in Pumby, the functionality of a particular unit that leads to good performance in HEK293FT and HeLa cells has been demonstrated. Pumby units at all positions in the assembly can bind to all four RNA bases, and the RNA bases flanking the target sequence do not affect binding. Protein binding to arbitrary RNA targets is a general ability with potentially infinite specific applications a few of which have been explored as relevant demonstrations. PumHD and Pumby binding to particular RNA sequences can mediate the reconstitution of split proteins. In the case of mRNA, furthermore, this signal is proportional to the mRNA molecule's rate of translation. This feature was used to measure the rate of translation of particular transcripts in living cells. PumHD and Pumby can also bring arbitrary proteins into contact with particular RNA sequences. This feature was used to mediate the silencing of RNA transcripts in living cells, and also to initiate the translation of arbitrary RNA coding sequences. In the broadest sense, PumHD and Pumby can scaffold proteins in living cells by placing them in a certain 2D or 3D order that is programmable with the sequence of the template mRNA.

Previous works with Pumilio proteins have demonstrated binding to point mutants of the wild-type Pumilio binding sequence. The presently disclosed PumHD technology, which is based on a different approach for modifying Pumilio specificity, is the first to show binding to arbitrary RNA sequences. The Pumby technology is the first to demonstrate protein binding to arbitrary RNA sequences of varying length. Binding to arbitrary RNA sequences has two primary advantages over previous sequence-specific RNA binding proteins. First, the ability to bind to individual RNA molecules extends to all molecules in the cell, not just those that include a very specific target sequence. Since arbitrary protein effector domains can be attached to PumHD and Pumby, this means that arbitrary proteins may be brought in contact with particular RNA targets in the cell. This is a very general capability, some instances of which have been demonstrated; including detection of the presence of individual RNA molecules, measurement of their translation rates, silencing of them through nuclease activity, and initiating their translation by creating virtual ribosomal entry sites. Being able to provide arbitrary binding sequences also means that a practically unlimited supply of programmable protein-RNA pairs can now be used for in-vivo scaffolding applications, and carefully designed strands of RNA can now be used to organize multiple proteins in a specific order in two or three dimensions, with a complexity not attainable with sequence-specific binding proteins.

Development of model through systematic assessment of on-target vs. off-target PumHD variant binding.

The wild-type PumHD protein is a natural RNA binding protein 110 that binds natively to the 8-nucleotide Nanos Response Element (NRE) RNA sequence 120, as shown in FIG. 1, which depicts the crystal structure of the wild-type human Pumilio Homology Domain (PumHD) with its cognate RNA (PDB 1M8X) [Wang X, McLachlan J, Zamore P D, Hall T M T (2002) Modular Recognition of RNA by a Human Pumilio-Homology Domain. Cell 110(4):501-512].

Figure 2:
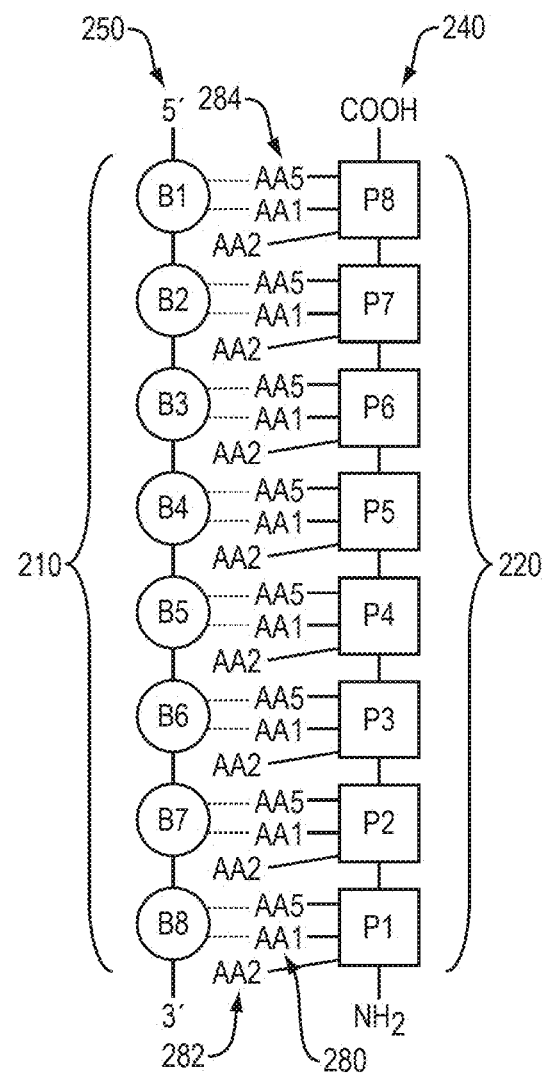
FIG. 2 is a schematic representation of RNA bases binding to their respective PumHD protein units.

The 8 key units of PumHD make direct hydrogen bond contacts with the corresponding RNA bases of the NRE, via three key amino acids in each unit, as shown in FIG. 2, which is a schematic representation of RNA bases 210 (labeled B1 to B8) binding to their respective PumHD protein units 220 (labeled P8 to P1). Note the reversed binding direction: the carboxy terminus 240 of the Pum protein binds to the 5' end 250 of the target RNA. Three amino acids 280, 282, 284 (labeled AA1, AA2, and AA5) are key for recognizing the target nucleobases.

Previous efforts have revealed how specific units within PumHD bind to their cognate RNA bases within NRE, at a structural level, and also PumHD variants have been mutated so that the binding specificity of one or more units is altered, to facilitate binding to NRE mutants. The wild-type PumHD does not bind C, although molecular engineering has shown that some of the Pum units can be mutated to bind C with good yield and specificity [Dong, S. et al. Specific and modular binding code for cytosine recognition in Pumilio/FBF (PUF) RNA-binding domains. The Journal of biological chemistry 286, 26732-26742 (2011)]. Based on these references, the most popular choices for each unit were analyzed, when mutants were available, in order to assemble a literature-derived consensus sequence that describes how the wild-type PumHD could be mutated so that any unit could bind any base. FIG. 3 depicts the literature-derived consensus sequence for how to change PumHD so that any unit could bind any base. In FIG. 3, each entry 310 (1-8) contains a proposed choice of AA1 310, AA2 320, and AA5 330 for the indicated PumHD unit to bind the indicated RNA base 330.

A wide number of studies have mutated different units of PumHD to bind different target bases, testing various mutations in various cell-free or cellular contexts. Eleven of these studies used mammalian cells to explore 12 out of the 18 possible combinations of mutant units and their target bases that differ from the wild-type.

Since no single study had tested PumHD variants binding to all 4 possible nucleotides at each unit's position under the same set of conditions, first it was systematically assessed whether all PumHD single-unit mutants could target their respective 8-nucleotide sequences. An assay commonly used in Pumilio evaluation, and also useful in cell biology, mammalian cell RNA-based GFP complementation, was used to accomplish this. This assay is qualitative, not fully quantitative, but is useful because it is what end-users in cell biology often use when attempting to answer scientific questions about the presence, absence, or general magnitude of a transcript, or even co-localization of a transcript with something else. GFP reconstitution has, accordingly, been widely used in the study of RNA binding proteins such as Pumilio and its variants [Ozawa T, Natori Y, Sato M, Umezawa Y (2007) Imaging dynamics of endogenous mitochondrial RNA in single living cells. Nat Methods 4(5):413-419; Yamada T, Yoshimura H, Inaguma A, Ozawa T (2011) Visualization of nonengineered single mRNAs in living cells using genetically encoded fluorescent probes. Anal Chem 83(14):5708-5714; Yoshimura H, Inaguma A, Yamada T, Ozawa T (2012) Fluorescent probes for imaging endogenous β-actin mRNA in living cells using fluorescent protein-tagged pumilio. ACS Chem Biol 7(6):999-1005; Tilsner J, et al. (2009) Live-cell imaging of viral RNA genomes using a Pumilio-based reporter. Plant J 57(4):758-770].

A Golden Gate assembly method was adapted from the TAL effector field to rapidly create PumHD variants. The split fluorescent protein reconstitution assay (here, GFP) previously used to test on-target binding of three different Pum variants to NRE variants (and also previously used to visualize binding of PumHD variants to the mRNAs for human beta actin and NADH dehydrogenase subunit 6) [Ozawa T, Natori Y, Sato M, Umezawa Y (2007) Imaging dynamics of endogenous mitochondrial RNA in single living cells. Nat Methods 4(5):413-419; Yamada T, Yoshimura H, Inaguma A, Ozawa T (2011) Visualization of nonengineered single mRNAs in living cells using genetically encoded fluorescent probes. Anal Chem 83(14):5708-5714; Yoshimura H, Inaguma A, Yamada T, Ozawa T (2012) Fluorescent probes for imaging endogenous β-actin mRNA in living cells using fluorescent protein-tagged pumilio. ACS Chem Biol 7(6):999-1005; Tilsner J, et al. (2009) Live-cell imaging of viral RNA genomes using a Pumilio-based reporter. Plant J 57(4):758-770] was adapted, as shown in FIGS. 4 and 5.

Figure 4:
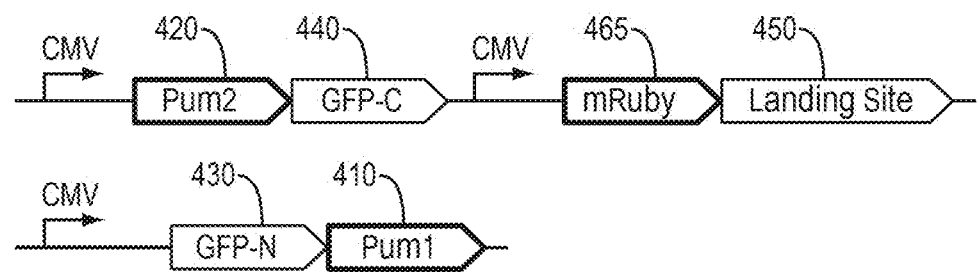
FIG. 4 is a schematic of the plasmids used in the binding assay for validating the PumHD consensus sequence of the panel shown in FIG. 3.
Figure 5:
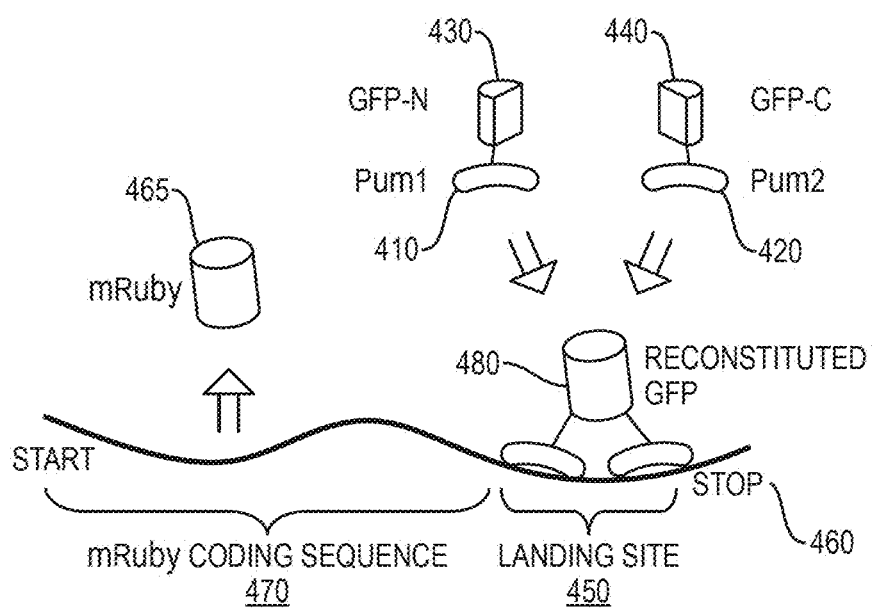
FIG. 5 is a schematic of the binding event that results from usage of the plasmids shown in FIG. 4.

FIG. 4 is a schematic of the plasmids used in the binding assay for validating the PumHD consensus sequence of the panel shown in FIG. 3. FIG. 5 depicts the binding event that results from usage of the plasmids shown in FIG. 4. Shown in FIGS. 4 and 5 are PumHD variant 410 (denoted Pum1) and wild-type PumHD 420 (denoted Pum2), which are each fused to one part of split GFP 430, 440. Each of them targets one 8-mer binding site within the landing site 450 inserted before the stop codon 460 of mRuby 465. The mRuby-landing site fusion transcript 470 serves as a scaffold for GFP reconstitution 480 upon PumHD binding, and the mRuby protein provides a control for overall cell density and transfection efficiency.

Figure 6:
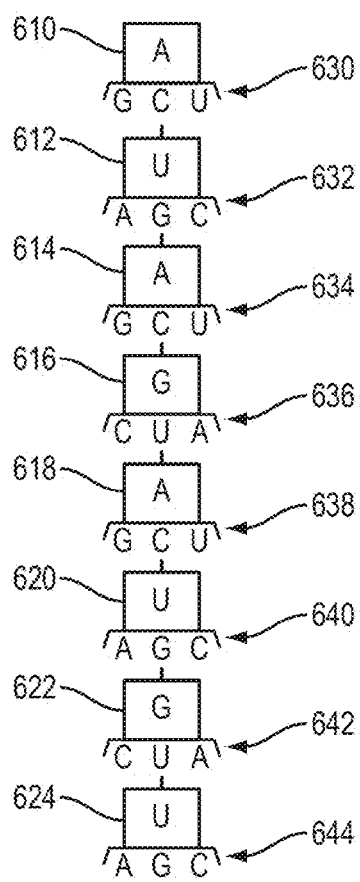
FIG. 6 depicts a schematic representation of the RNA bases recognized by the "reference PumHD mutant", which binds the target sequence used in an example GFP reconstitution study.

Every unit of a specific reference PumHD variant was mutated, in order to test each unit's binding to each of the four RNA bases (FIG. 6) according to the hypothesized consensus sequences (FIG. 3). FIG. 6 depicts a schematic representation of the RNA bases recognized by the "reference PumHD mutant", which binds the target sequence used in the GFP reconstitution study of Ozawa et al. [Ozawa T, Natori Y, Sato M, Umezawa Y (2007) Imaging dynamics of endogenous mitochondrial RNA in single living cells. Nat Methods 4(5):413-419]. The bases of the reference PumHD mutant are large letters in squares 610, 612, 614, 616, 618, 620, 622, 624, as well as variants in which each unit of the reference PumHD mutant is, in turn, mutated to the consensus unit that binds each possible base (small letters under the squares).

The reference PumHD variant, which binds 3'-AUA-GAUGU-5', had been characterized in a previous reconstitution study. Throughout the experiments, two PumHD proteins were used, each fused to one part of a split GFP, which bind next to each other right before the stop codon of a transcript that codes for mRuby (with a few extra bases added to form a landing site for the PumHD proteins; see FIG. 5). Each new PumHD mutant (denoted Pum1) would be expressed alongside the same reference PumHD (denoted Pum2). One of the two target RNA sequences would always match its protein (usually Pum2, but see Table 1), whereas the other target RNA sequence would vary to either match ("on-target" experiments) or not match ("off-target" experiments) the protein. The off-target mRNA sequences were created by swapping each purine in the sequence with a pyrimidine, and vice versa. Table 1 presents a list of sequences of Pum proteins used in the described experiments.

TABLE 1

| Label | Pum1 | Pum2 |
|---|---|---|
| SWAP | AUAGAUGU | GCGAGCAC |
| 1-G | GUAGAUGU | AUAUAUGU |
| 1-C | CUAGAUGU | AUAUAUGU |
| 1-U | UUAGAUGU | AUAUAUGU |
| 2-A | AAAGAUGU | AUAUAUGU |
| 2-G | AGAGAUGU | AUAUAUGU |
| 2-C | ACAGAUGU | AUAUAUGU |
| 3-G | AUGGAUGU | AUAUAUGU |
| 3-C | AUCGAUGU | AUAUAUGU |
| 3-U | AUUGAUGU | AUAUAUGU |
| 4-C | AUACAUGU | AUAUAUGU |
| 4-U | AUAUAUGU | GCGAGCAC |
| 4-A | AUAAAUGU | AUAUAUGU |
| 5-G | AUAGGUGU | AUAUAUGU |
| 5-C | AUAGCUGU | AUAUAUGU |
| 5-U | AUAGUUGU | AUAUAUGU |
| 6-A | AUAGAAGU | AUAUAUGU |
| 6-G | AUAGAGGU | AUAUAUGU |
| 6-C | AUAGACGU | AUAUAUGU |
| 7-C | AUAGAUCU | AUAUAUGU |
| 7-U | AUAGAUUU | AUAUAUGU |
| 7-A | AUAGAUAU | AUAUAUGU |
| 8-A | AUAGAUGA | AUAUAUGU |
| 8-G | AUAGAUGG | AUAUAUGU |
| 8-C | AUAGAUGC | AUAUAUGU |
| A NRE G | AUAUAUGU | GCGAGCAC |
| G NRE C | AUAUAUGU | GCGAGCAC |
| C NRE U | AUAUAUGU | GCGAGCAC |
| U NRE A | AUAUAUGU | GCGAGCAC |

Figure 7A:
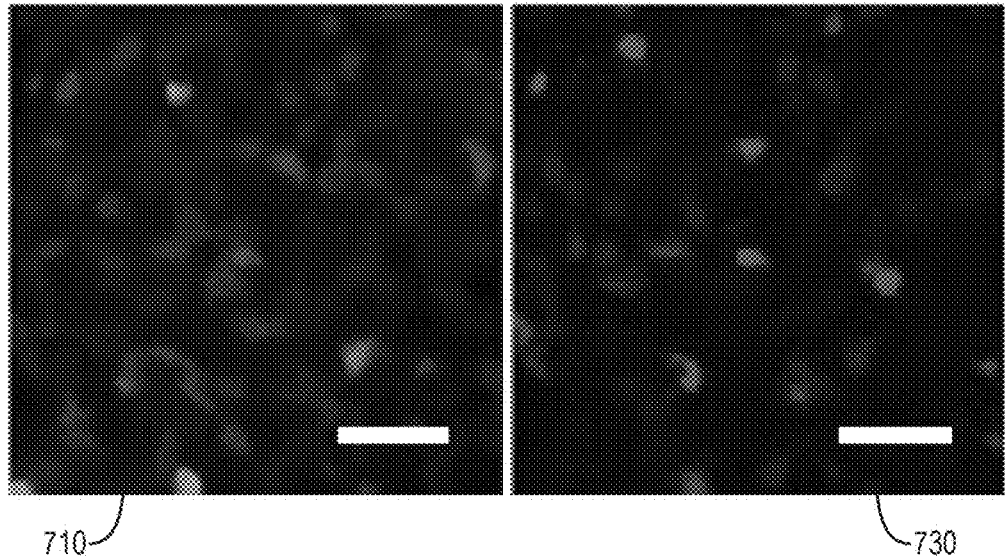
FIG. 7A depicts representative fluorescent microscopy images of HEK293FT cells expressing the system of FIG. 4, with a Pum1 that is on-target with respect to its mRNA binding site.
Figure 7B:
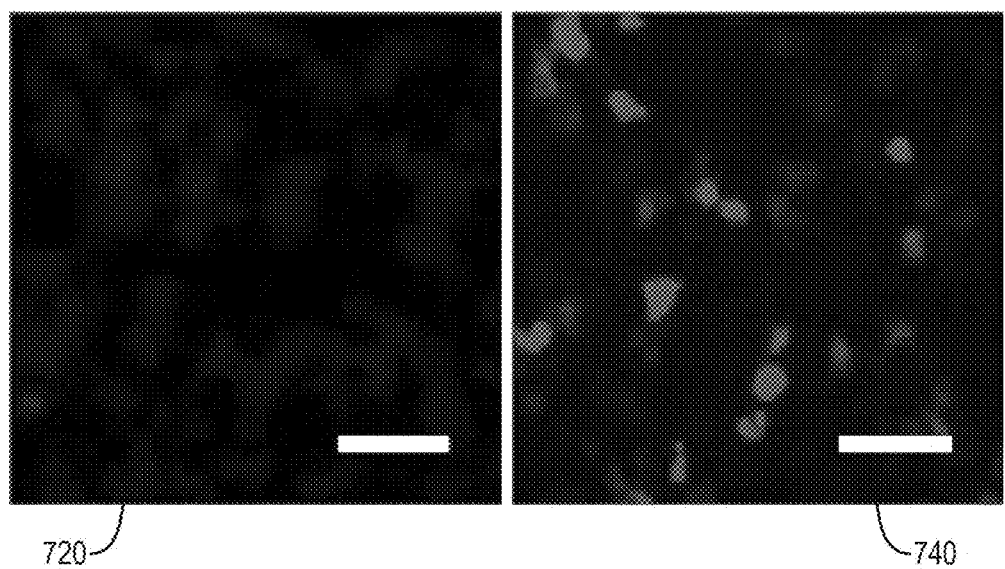
FIG. 7B depicts representative fluorescent microscopy images of HEK293FT cells expressing the system of FIG. 4, but for a Pum1 variant that is off-target with respect to its co-transfected mRNA binding site.

Since one of the protein-mRNA pairs was known to bind in each experiment, overall GFP reconstitution was determined by the binding effectiveness of the other pair: effective binding lead to ample green fluorescence 710, as shown in FIG. 7A and poor binding did not 720, as shown in FIG. 7B, as measured against a constant amount of red fluorescence 730, 740 given by constant mRuby expression. FIG. 7A depicts representative fluorescent microscopy images of HEK293FT cells expressing the system of FIG. 4, with a Pum1 that is on-target with respect to its mRNA binding site, along with the mRuby expression control. FIG. 7B depicts representative fluorescent microscopy images of HEK293FT cells expressing the system of FIG. 4, but for a Pum1 variant that is off-target with respect to its co-transfected mRNA binding site. Scale bars, 100 μm.

Figure 8:
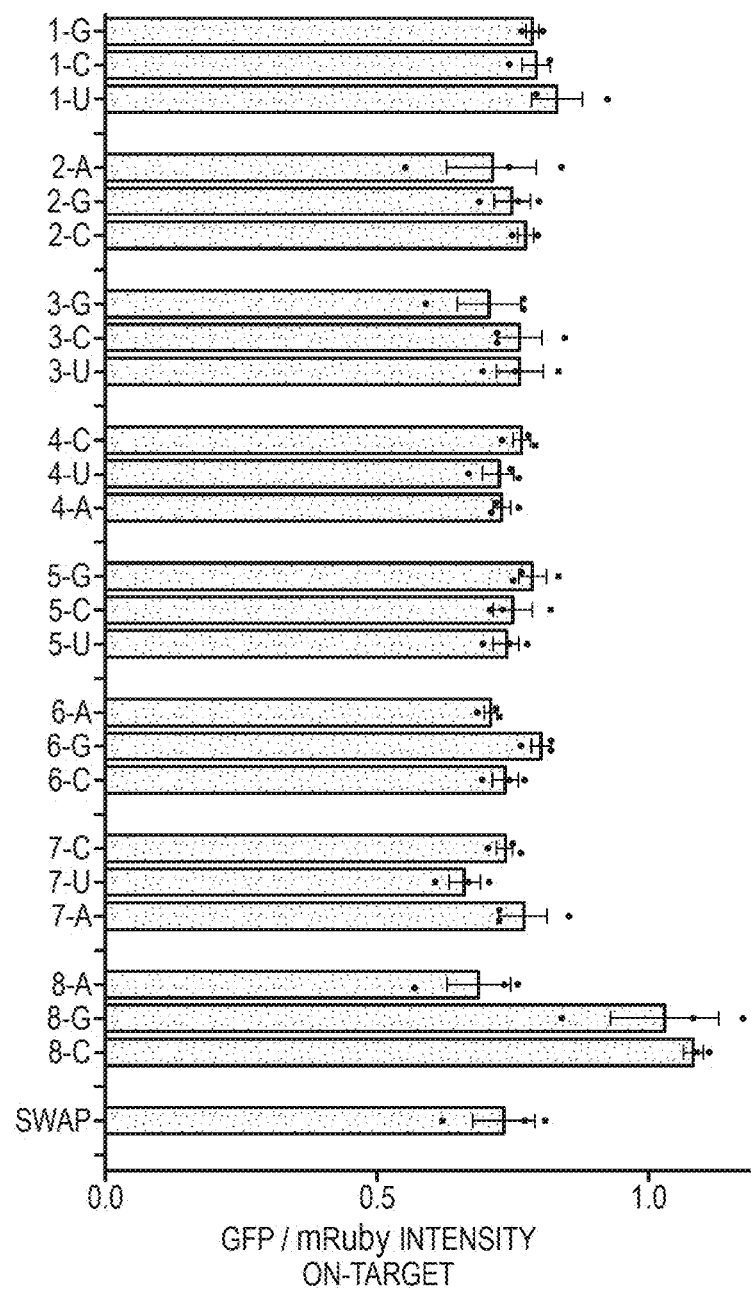
FIG. 8 depicts the ratio of reconstituted GFP intensity to mRuby intensity for PumHD variants tested with on-target mRNAs.
Figure 9:
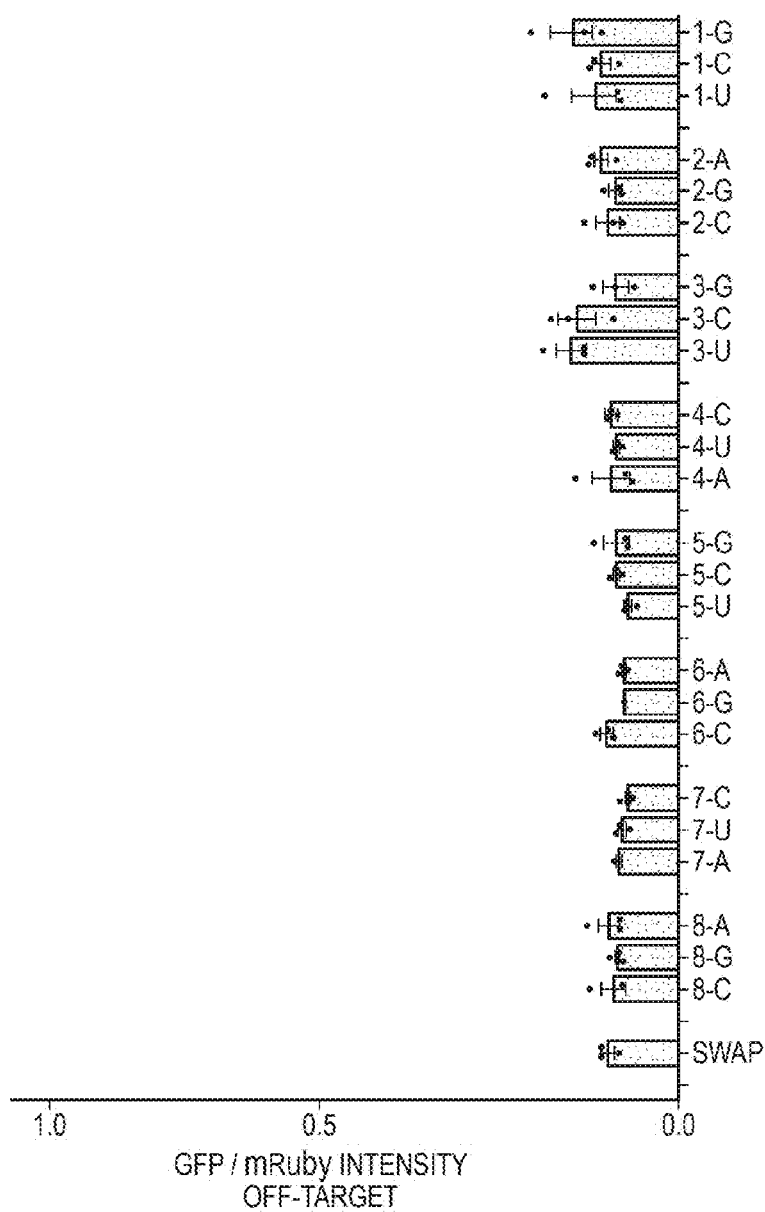
FIG. 9 depicts the ratio of reconstituted GFP intensity to mRuby intensity for PumHD variants paired with mRNAs generated to assess off-target effects.

The graphs in FIGS. 8 and 9 compare the amount of green fluorescence, normalized to the constant red fluorescence, for on- vs. off-target sequences, respectively. FIG. 8 depicts the ratio of reconstituted GFP intensity to mRuby intensity for PumHD variants tested with on-target mRNAs. Each bar represents an experiment in which the reference PumHD mutant was further mutated to recognize a different RNA base at that position, as indicated in FIG. 6. FIG. 9 depicts the ratio of reconstituted GFP intensity to mRuby intensity for PumHD variants paired with mRNAs generated to assess off-target effects. It was found that on-target Pum binding resulted in significantly higher GFP reconstitution compared to off-target binding ($P<0.0001$; all reported P-values throughout this disclosure are for ANOVAs unless otherwise specified), with on-target binding presenting a GFP/mRuby ratio on average 6.1-fold greater (standard deviation of 1.37 fold) than the corresponding ratio for off-target binding. The behavior of 24 PumHD variants that differed by one target sequence base from the original was tested, confirming that they all exhibited the same binding behavior ($P>0.05$, ANOVA with Dunnett's post hoc test using wild-type, i.e., 4-U-PumHD as the reference). Thus, as expected given the prior literature, PumHD can indeed support any unit binding any base.

Figure 10:
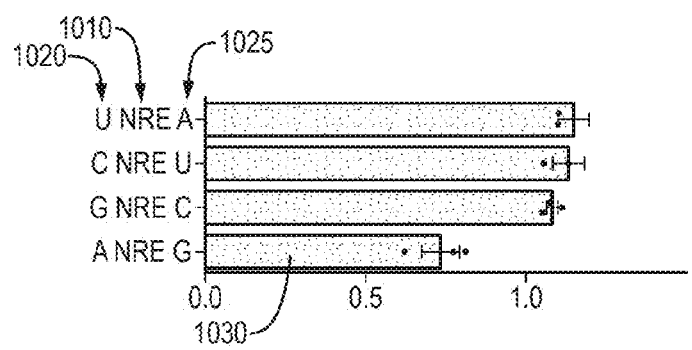
FIG. 10 presents GFP/mRuby ratios for wild-type PumHD tested against the wild-type NRE flanked by different adjacent nucleotides.

Although PumHD variants have been widely used in a variety of contexts, no previous study had taken a single PumHD variant and explored whether multiple different up- and down-stream bases (5' and 3' from the 8-mer target sequence, respectively) affect binding of that Pum protein. The results of testing binding of the wild-type PumHD in the case of the upstream and the downstream base being either A, U, C, or G, investigated in pairs: upstream U—downstream A, upstream C—downstream U, upstream G—downstream C, and upstream A—downstream G, are shown in FIG. 10, which presents GFP/mRuby ratios for wild-type PumHD tested against the wild-type NRE 1010 flanked by different adjacent nucleotides 1020, 1025. The bar at bottom, A NRE G 1030, is for the pair of flanking bases used in the previous graphs. Values throughout are mean±s.e.m.

All of the variants in upstream and downstream bases yielded qualitatively similar successful binding although, numerically, there were statistically significant differences in the magnitude of the GFP reconstitution detected. Given that any protein-RNA interaction will be susceptible to environmental changes, e.g. secondary structure arising from the specific sequences involved, this result suggests that PumHD variants should be vetted on a per-case basis. However, PumHD variants were generally capable of binding their target regardless of the bases immediately upstream and downstream of the core 8 bases, which is important for general bioengineering application of PumHD variants.

A Modular Protein Architecture for RNA Binding.

Next, a set of four canonical protein modules were devised, each of which targets one RNA base with high specificity and fidelity. For simplicity, AA2 (the "stacking" amino acid) was kept the same for all 4 modules. Since most of the PumHD units of FIG. 3 had either Y or R for AA2, unit 7 was eliminated from consideration. Which units had been most thoroughly mutated by the most groups was examined, resulting in units 3 and 6 of the PumHD scaffold of FIG. 3 being selected as candidate Pumby module starting material. Variants of units 3 and 6 were then screened using the process described previously.

Using unit 3 and stacking amino acid R, the tested assemblies of 6 or 8 units appeared to hamper cell survival. Using unit 3 and stacking amino acid Y, the tested assemblies of 6 or 8 units did not hamper cell survival, but no Pum-mediated GFP reconstitution was observed. Using unit 6 and stacking amino acid R, it was found that the tested assemblies of 6, 8, and 10 units expressed well in HEK293FT and HeLa cells, but very weak Pum-mediated GFP reconstitution was observed for all tested sequences. Finally, testing unit 6 with stacking amino acid Y found normal cell health and also GFP reconstitution, which resulted in the presently disclosed Pumby (Pumilio-based assembly) module.

Figures 11A, 11B:
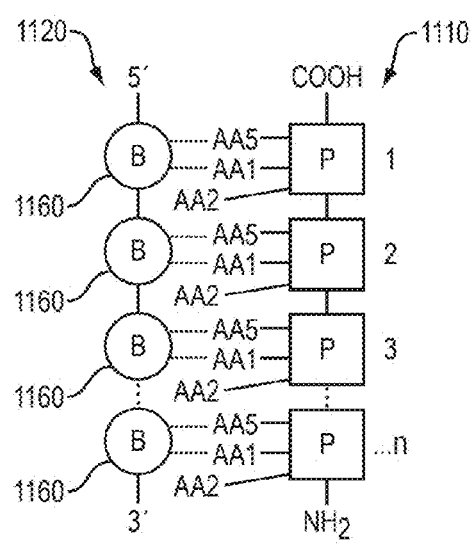
FIG. 11A is a schematic representation of a modular protein architecture for RNA binding according to one aspect of the invention, wherein concatenated chains of stereotyped Pumilio modules can bind target RNAs of variable length and sequence.
FIG. 11B depicts a universal set of 4 modules, called Pumby (Pumilio-based Assembly), each of which can bind one RNA base when situated in any location in the chain of FIG. 11A, according to one aspect of the invention.

FIG. 11A is a schematic representation of a modular protein architecture for RNA binding according to one aspect of the invention, wherein concatenated chains 1110 of stereotyped Pumilio modules can bind target RNAs 1120 of variable length and sequence. FIG. 11B depicts a universal set of 4 modules 1130, 1135, 1140, 1145, called Pumby modules, each of which can bind one RNA base 1160 when situated in any location in the chain of FIG. 11A.

Figure 12A:
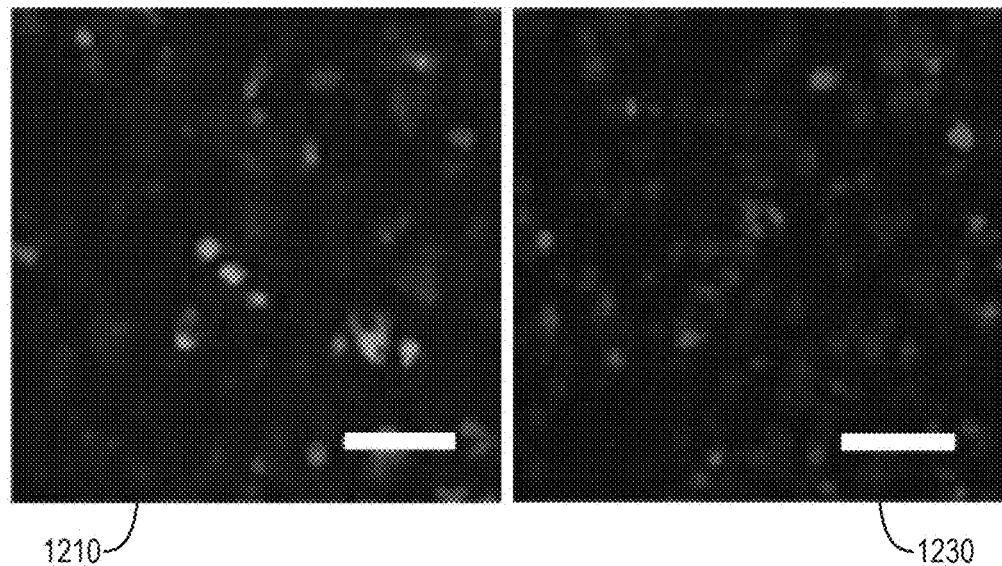
FIG. 12A depicts representative fluorescent microscopy images of HEK293FT cells expressing the system of FIG. 11A, using the vector strategy of FIGS. 4 and 5.
Figure 12B:
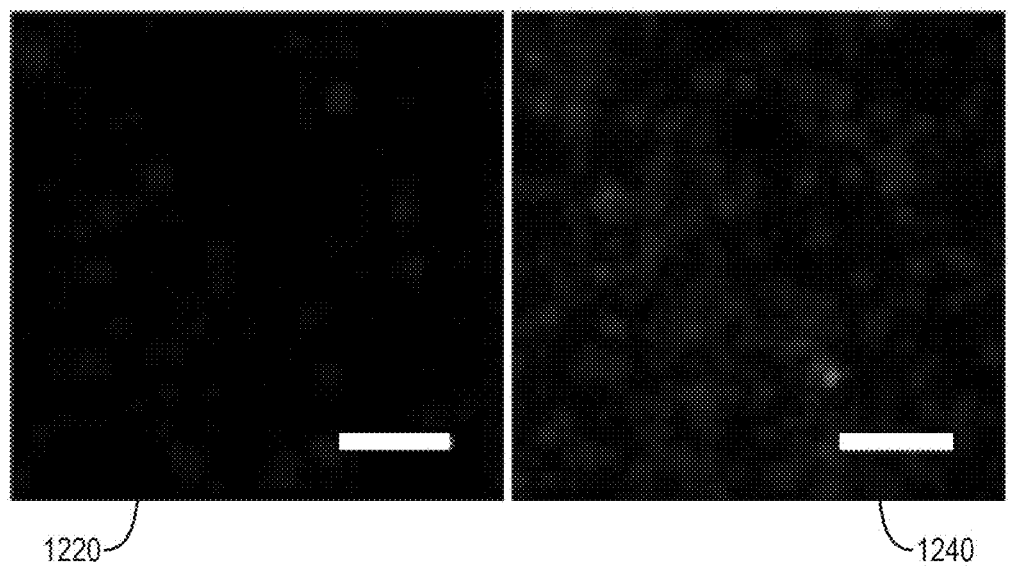
FIG. 12B depicts representative fluorescent microscopy images of HEK293FT cells expressing the system of FIG. 11A as in FIG. 12A, but for the case of an 8-mer Pumby chain off-target with respect to its co-transfected RNA binding site.

The performance of this set was systematically validated. As previously, both on-target and off-target binding in live mammalian cells were tested, using GFP reconstitution. It was found that on-target pairs yielded GFP, whereas off-target pairs did not, as shown in FIGS. 12A and 12B. FIG. 12A depicts representative fluorescent microscopy images of HEK293FT cells expressing the system of FIG. 11A, using the vector strategy of FIGS. 4 and 5. In this case, Pum1 is a 6-mer Pumby chain on-target with respect to its mRNA binding site 1210, and Pum2 is an 8-mer Pumby chain designed to target the same sequence as wild-type PumHD. FIG. 12B depicts representative fluorescent microscopy images of HEK293FT cells expressing the system of FIG. 11A as in FIG. 12A, but for the case of an 8-mer Pumby chain off-target with respect to its co-transfected RNA binding site 1220. The panels on the right show the mRuby expression controls 1230, 1240. Scale bars, 100 μm.

A full list of the target binding sequences used in this experiment are found in Tables 2-4, for Pumby 8mer (Table 2), Pumby 6mer (Table 3), and variable length Pumby (Table 4).

TABLE 2

Pumby 8 mer

| Label | Pum1 | Pum2 |
|---|---|---|
| SWAP | AUAGAUGU | GCGAGCAC |
| 1-G | GUAGAUGU | AUAUAUGU |
| 1-C | CUAGAUGU | AUAUAUGU |
| 1-U | UUAGAUGU | AUAUAUGU |
| 2-A | AAAGAUGU | AUAUAUGU |
| 2-G | AGAGAUGU | AUAUAUGU |
| 2-C | ACAGAUGU | AUAUAUGU |
| 3-G | AUGGAUGU | AUAUAUGU |

TABLE 2-continued

Pumby 8 mer

| Label | Pum1 | Pum2 |
|---|---|---|
| 3-C | AUCGAUGU | AUAUAUGU |
| 3-U | AUUGAUGU | AUAUAUGU |
| 4-C | AUACAUGU | AUAUAUGU |
| 4-U | AUAUAUGU | GCGAGCAC |
| 4-A | AUAAAUGU | AUAUAUGU |
| 5-G | AUAGGUGU | AUAUAUGU |
| 5-C | AUAGCUGU | AUAUAUGU |
| 5-U | AUAGUUGU | AUAUAUGU |
| 6-A | AUAGAAGU | AUAUAUGU |
| 6-G | AUAGAGGU | AUAUAUGU |
| 6-C | AUAGACGU | AUAUAUGU |
| 7-C | AUAGAUCU | AUAUAUGU |
| 7-U | AUAGAUUU | AUAUAUGU |
| 7-A | AUAGAUAU | AUAUAUGU |
| 8-A | AUAGAUGA | AUAUAUGU |
| 8-G | AUAGAUGG | AUAUAUGU |
| 8-C | AUAGAUGC | AUAUAUGU |
| A NRE G | AUAUAUGU | GCGAGCAC |
| G NRE C | AUAUAUGU | GCGAGCAC |
| C NRE U | AUAUAUGU | GCGAGCAC |
| U NRE A | AUAUAUGU | GCGAGCAC |

TABLE 3

Pumby 6 mer

| Label | Pum1 | Pum2 |
|---|---|---|
| SWAP | AUAGAU | GCGAGCAC |
| 1-G | GUAGAU | AUAUAUGU |
| 1-C | CUAGAU | AUAUAUGU |
| 1-U | UUAGAU | AUAUAUGU |
| 2-A | AAAGAU | AUAUAUGU |
| 2-G | AGAGAU | AUAUAUGU |
| 2-C | ACAGAU | AUAUAUGU |
| 3-G | AUGGAU | AUAUAUGU |
| 3-C | AUCGAU | AUAUAUGU |
| 3-U | AUUGAU | AUAUAUGU |
| 4-C | AUACAU | AUAUAUGU |
| 4-U | AUAUAU | AUAUAUGU |

TABLE 3-continued

Pumby 6 mer

| Label | Pum1 | Pum2 |
|---|---|---|
| 4-A | AUAAAU | AUAUAUGU |
| 5-G | AUAGGU | AUAUAUGU |
| 5-C | AUAGCU | AUAUAUGU |
| 5-U | AUAGUU | AUAUAUGU |
| 6-A | AUAGAA | AUAUAUGU |
| 6-G | AUAGAG | AUAUAUGU |
| 6-C | AUAGAC | AUAUAUGU |

TABLE 4 variable length Pumby

| Label | Pum1 | Pum2 |
|---|---|---|
| 6 mer | AUAUAU | AUAUAUGU |
| 7 mer | AUAUAUG | AUAUAUGU |
| 8 mer | AUAUAUGU | AUAUAUGU |
| 9 mer | AUAUAUGUA | AUAUAUGU |
| 10 mer | AUAUAUGUAA (SEQ ID No. 1) | AUAUAUGU |
| 11 mer | AUAUAUGUAAG (SEQ ID No. 2) | AUAUAUGU |
| 12 mer | AUAUAUGUAAGG (SEQ ID No. 3) | AUAUAUGU |
| 13-mer | AUAUAUGUAAGGC (SEQ ID No. 4) | AUAUAUGU |
| 14-mer | AUAUAUGUAAGGCG (SEQ ID No. 5) | AUAUAUGU |
| 15-mer | AUAUAUGUAAGGCGG (SEQ ID No. 6) | AUAUAUGU |
| 16-mer | AUAUAUGUAAGGCGGC (SEQ ID No. 7) | AUAUAUGU |
| 17-mer | AUAUAUGUAAGGCGGCU (SEQ ID No. 8) | AUAUAUGU |
| 18-mer | AUAUAUGUAAGGCGGCUU (SEQ ID No. 9) | AUAUAUGU |

Figure 13:
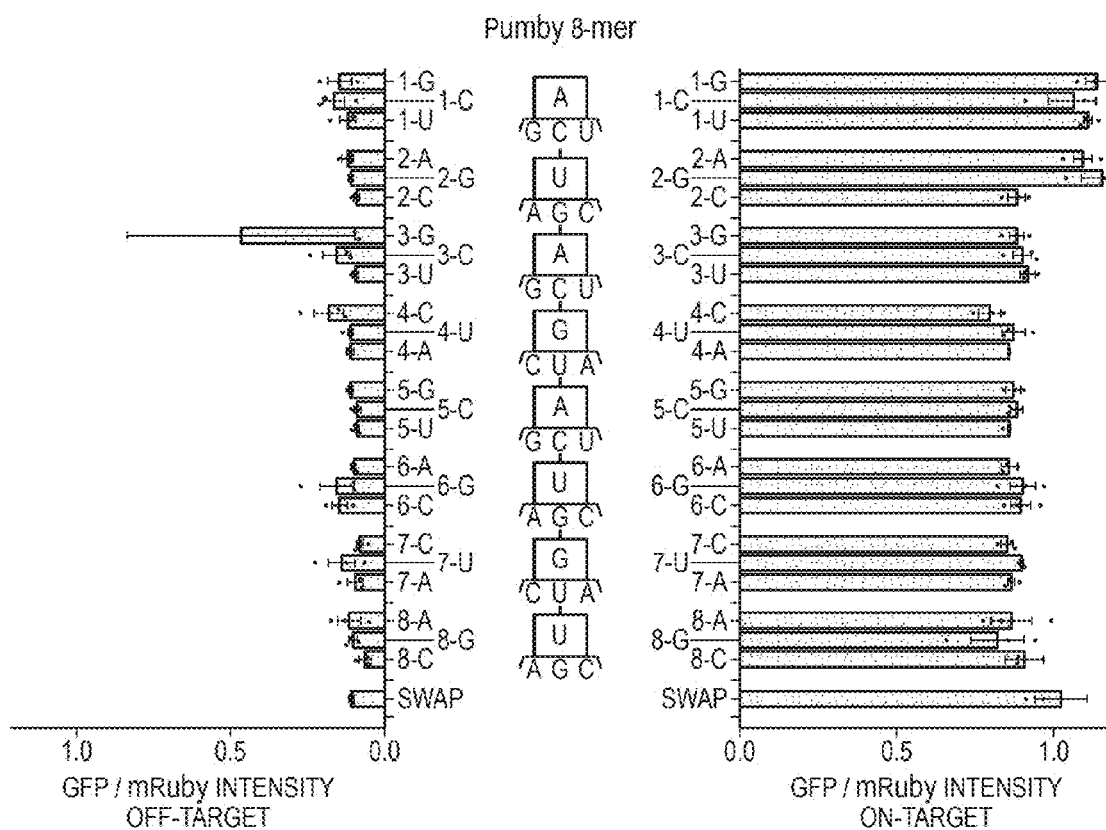
FIG. 13 illustrates on-target Pum binding results.

It was found that, for Pumby-based chains that were 8 units long (abbreviated Pumby8), on-target Pum binding resulted in significantly higher GFP reconstitution compared to off-target binding, as seen in FIG. 13 ($P<0.0001$), as it had for the previously-tested PumHD variants (FIGS. 6, 8, and 9), but instead for 8-mer Pumby chains.

Figure 14:
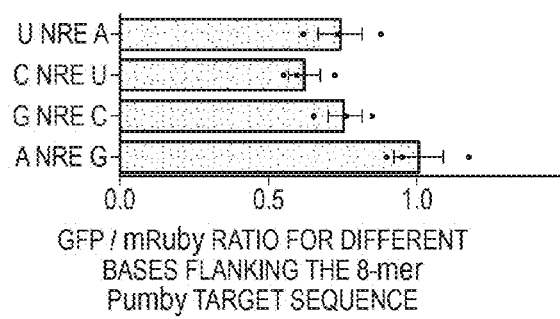
FIG. 14 presents results similar to those presented in FIG. 10, but for the 8-mer Pumby chain that binds to the wild-type NRE, being tested against the same 4 target RNAs with variable flanking bases.

Also explored was the effect of varying flanking bases around the Pumby target sequence (as for PumHD variants in FIG. 10), and again qualitatively similar successful binding along with statistically significant differences was found (FIG. 14). FIG. 14 presents results similar to those presented in FIG. 10, but instead for the 8-mer Pumby chain that binds to the wild-type NRE, tested against the same 4 target RNAs with variable flanking bases. Values throughout are mean±s.e.m.

Purified PumHD variants, as well as Pumby8 chains, were used to measure $K_d$ for on- vs. off-target pairs, obtaining $K_d$'s in the nanomolar range for both Pumby8 and PumHD variants. Off-target pairs had no detectable binding. Table 5 presents binding of PumHD variants and Pumby variants to cognate and noncognate RNA as measured via fluorescence anisotropy of the FAM-labeled RNA target.

TABLE 5

| Protein | Active fraction | Cognate RNA | $K_a$ | STDev $K_a$ | $K_d$ nM | Noncognate RNA |
|---|---|---|---|---|---|---|
| PumHD wild-type | 0.35 | UGUAUAUA | 1.13E+10 | ± 1.71e+009 | 0.088 | ACAUAUAU |
| PumHD_KD_1 | 0.34 | GUGCUCGC | 8.50E+09 | ± 9.46e+008 | 0.118 | CACGAGCG |
| PumHD_KD_2 | 0.22 | CAUGUCAG | 2.77E+09 | ± 2.97e+008 | 0.362 | GUACAGUC |
| Pumby8_KD_3 | 0.27 | UGUAGAUA | 7.44E+08 | ± 2.71e+008 | 1.343 | ACAUCUAU |
| Pumby8_KD_4 | 0.26 | CAUGUCAG | 2.28E+09 | ± 1.71e+009 | 0.439 | GUACAGUC |

Figure 15:
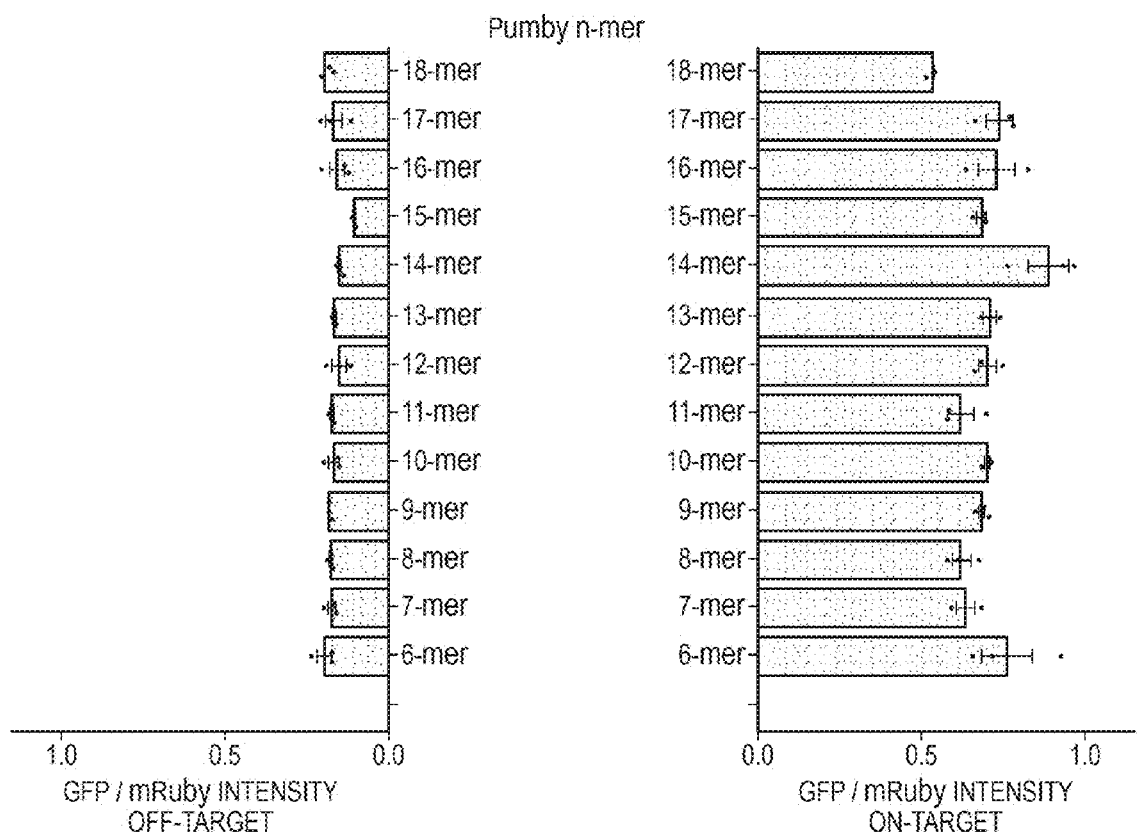
FIG. 15 presents results similar to those in FIG. 13, but for Pumby chains of varying length.

Having demonstrated the performance of Pumby chains 8 units long, Pumby chains that could bind to shorter or longer RNA sequences were also sought. Pumby chains ranging in length from 6 all the way to 18 units long (i.e., "Pumby6" to "Pumby18") were explored. It was found that, for Pumby-based chains of variable length, on-target Pum binding resulted in significantly higher GFP reconstitution compared to off-target binding, as seen in FIG. 15 (P<0.0001), which presents results similar to those in FIG. 13, but instead for Pumby chains of varying length. The 18-mer chain was tested against the sequence UUCGGCGGAAUGAUGGUU (SEQ ID No. 1), the 6-mer assembly was tested against AUGGUU, and all other assemblies were tested against intermediate truncations of the 18-mer target sequence. All of the Pumby chains ranging from length 6 to length 18 were indistinguishable from Pumby8 in terms of their GFP reconstitution effects, with one variant (length 14) significantly enhanced in binding vs. Pumby8 (P>0.05, ANOVA with Dunnett's post hoc test). Thus, Pumby modules can indeed support the generation of RNA binding proteins that are specific and that are longer in length than wild-type PumHD, that have efficacy comparable to the 8-mer Pumby (FIG. 13).

The stability of Pumby proteins compared to PumHD proteins that bind the same RNA target sequence was also investigated. A thermal assay, measuring fluorescence of SYPRO Orange as it is bound by unfolding protein, was used. The resulting melting curves show that all Pum variants have $T_m$ between 50-60° C., Pumby and PumHD alike.

Figure 16:
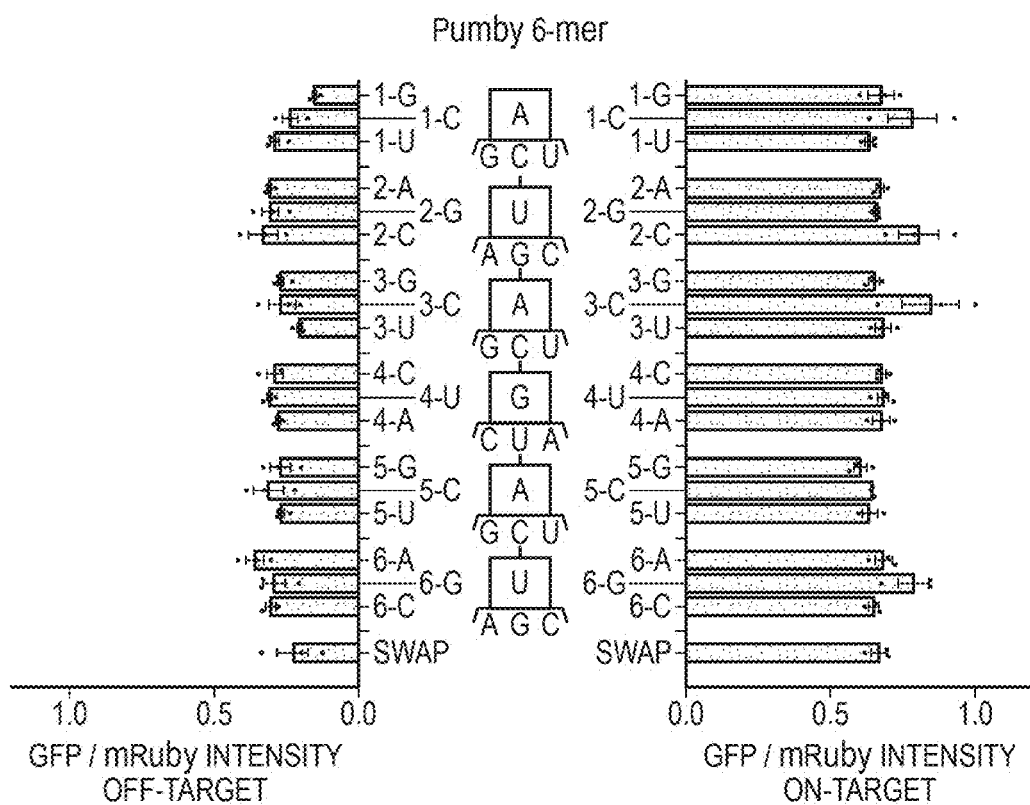
FIG. 16 presents results similar to that of FIG. 13, but for 6-mer Pumby chains.

Sequences shorter than Pumby8, synthesizing and testing Pumby chains that were 6 units long (i.e., Pumby6) were examined. Such chains also exhibited on-target Pum binding significantly higher than off-target binding, as shown in FIG. 16 (P<0.0001), which presents results similar to that of FIG. 13, but instead for 6-mer Pumby chains, using as targets the 6 bases bound by the first 6 units of the "reference PumHD mutant" (which binds the target sequence used in the GFP reconstitution study of Ozawa et al. [Ozawa T, Natori Y, Sato M, Umezawa Y (2007) Imaging dynamics of endogenous mitochondrial RNA in single living cells. Nat Methods 4(5):413-419]; the bases of the reference PumHD mutant are large letters in squares), and varying each base to the other 3 nucleotides. All of the Pumby6 variants explored had no significant difference in the magnitude of on vs. off-target change, when compared to the 4-U variant—i.e., the equivalent of the truncated wild-type, which was assessed in FIG. 15.

Modular RNA binding protein-based monitoring of RNA presence and translation.

Many pioneering demonstrations have been previously performed using wild-type PumHD (or variants thereof) to perform measurements or perturbations of RNA [Lunde B M, Moore C, Varani G (2007) RNA-binding proteins: modular design for efficient function. Nat Rev Mol Cell Biol 8(6):479-90; Mackay J P, Font J, Segal D J (2011) The prospects for designer single-stranded RNA-binding proteins. Nat Struct Mol Biol 18(3):256-61; Auweter S D, Oberstrass F C, Allain F H-T (2006) Sequence-specific binding of single-stranded RNA: is there a code for recognition? Nucleic Acids Res 34(17):4943-59; Choudhury R, Wang Z (2014) Manipulation of RNA using engineered proteins with customized specificity. Adv Exp Med Biol 825:199-225].

It was tested whether the modular Pumby architecture could enable equally valid measurements and perturbations of RNA. Pumby8 chains were compared to mutated PumHD proteins, in a variety of contexts familiar in the Pumilio literature, in order to validate the single-module design. For the first test, the Activating Transcription Factor 4 (ATF4) mRNA, whose transcription and translation is induced by cell exposure to thapsigargin, was chosen as a Pum target [Dey S, et al. (2010) Both transcriptional regulation and translational control of ATF4 are central to the integrated stress response. J Biol Chem 285(43):33165-74; Whitney M L, Jefferson L S, Kimball S R (2009) ATF4 is necessary and sufficient for ER stress-induced upregulation of REDD1 expression. Biochem Biophys Res Commun 379(2):451-5].

Figure 17:
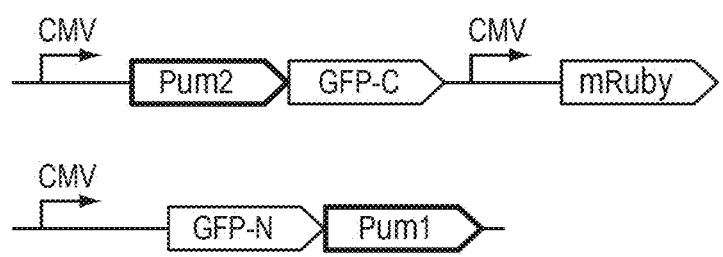
FIG. 17 depicts a schematic of reporter plasmid as in FIG. 4, but with Pum1 and Pum2 aimed at target sites in the mRNA for ATF4.

Using Pum-anchored split GFP targeted to different parts of the ATF4 gene, as shown in FIG. 17, protein production levels in living cells was longitudinally estimated. FIG. 17 depicts a schematic of the reporter plasmids, as in FIG. 4, but instead with Pum1 and Pum2 aimed at target sites in the mRNA for ATF4. All Pums, both Pumby and PumHD), used in the experiments in FIG. 17, target 8-mer RNA sequences. Pum target sites were uniquely identified for easy reference as PumHD_TM or Pumby8_TM, where TM stands for "transcript monitoring".

A full list of the target binding sequences used in the experiments of FIG. 17 is presented Table 6. Each mRNA target site contains two 8-base binding sites, one for each of the two Pum proteins needed to reconstitute a split reporter protein: Pum1 (N terminal fusion with split luciferase (Luc) or split GFP) binds to the binding site whose name ends in "A"; Pum2 (C terminal fusion with split luciferase or split GFP) binds to the binding site whose name ends in "B".

TABLE 6

| Label for the target site, as used in FIG. 13 | Names for the two constituent binding sites | mRNA target | Protein fused to Pum |
|---|---|---|---|
| 1 | Pumby8_TM_1A | ACGGCCAC | N-Luc |
|   | Pumby8_TM_1B | CAGCGUGU | C-Luc |
| 2 | PumHD_TM_2A | GAAGGCUA | N-Luc |
|   | PumHD_TM_2B | AGGAGCGC | C-Luc |
| 3 | Pumby8_TM_3A | GCCCGACA | N-Luc |
|   | Pumby8_TM_3B | UACCUGAG | C-Luc |
| 4 | Pumby8_TM_4A | CUGCUGUG | N-Luc |
|   | Pumby8_TM_4B | CAGUGUUG | C-Luc |
| 5 | Pumby8_TM_5A | GAGCGACA | N-Luc |
|   | Pumby8_TM_5B | GCGGCUAA | C-Luc |
| 6 | PumHD_TM_6A | GACAACAG | N-Luc |
|   | PumHD_TM_6B | CGAUUGGA | C-Luc |
| 7 | PumHD_TM_7A | UGAGCUUC | N-GFP |
|   | PumHD_TM_7B | CAGCGAGG | C-GFP |
| 8 | Pumby8_TM_8A | GACAGAUU | N-GFP |
|   | Pumby8_TM_8B | UUGGAGAA | C-GFP |
|   | PumHD_TM_9A | AUAGGUGU | N-GFP |
|   | PumHD_TM_9B | GCGAGCAC | C-GFP |

Figure 18:
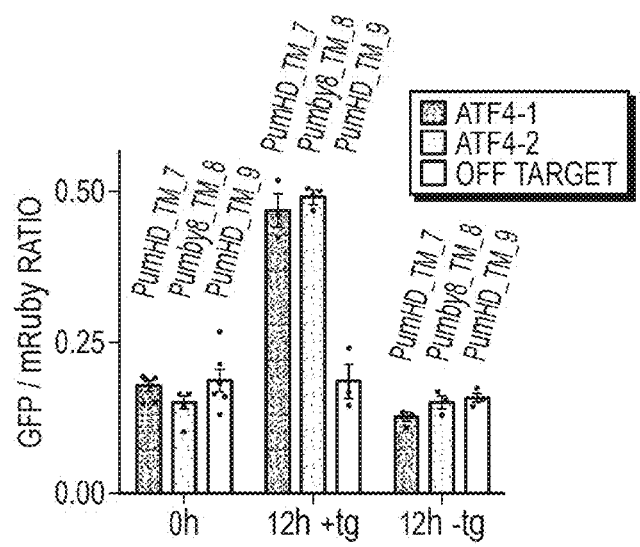
FIG. 18 depicts Pum-guided GFP reconstitution using the reporters of FIG. 17.

Significant differences of Pum-mediated GFP reconstitution in response to thapsigargin were observed, as shown in FIG. 18 (P<0.0001, ANOVA with Tukey's post hoc test). Shown in FIG. 18, is Pum-guided GFP reconstitution using the reporters of FIG. 17. "Time 0" represents the beginning of the experiment (6 biological replicates). Half of the samples (3 biological replicates) were exposed to thapsigargin (+tg), half were not (−tg), and both were imaged 12 hours later. Error bars are s.e.m.

Figure 19:
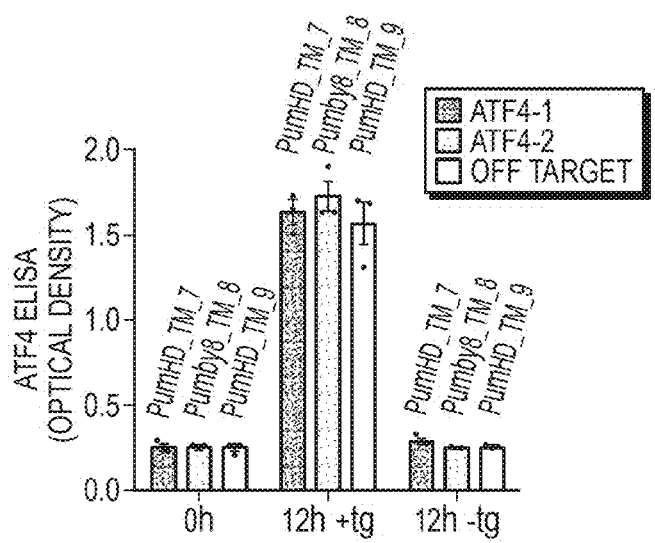
FIG. 19 shows that increases in Pum-mediated GFP reconstitution were associated with qualitative increases in the ATF4 protein.

The increases in Pum-mediated GFP reconstitution were associated with qualitative increases in the ATF4 protein, as measured by ELISA and shown in FIG. 19 (P<0.0001, ANOVA with Tukey's post hoc test) for samples prepared as those in FIG. 18. No significant difference in performance was observed between Pumby8 and PumHD in this assay (FIG. 18, P=0.3248). Error bars are s.e.m.

Translation Monitoring.

A novel use of programmable RNA binding proteins was developed: monitoring of translation in live cells. Initial experiments showed how Pum proteins can recruit split GFP to produce green fluorescence in the presence of a target RNA (as in FIG. 5). This useful result was only observed, however, when the target site was located within an open reading frame. Putting a stop codon upstream of the target site resulted in no detectable GFP reconstitution. It was hypothesized that, in the former case, ribosomal translation repeatedly displaces Pum-bound reconstituted GFP and allows for new split GFP halves to be bound and reconstituted. Higher translation, thus, would produce a greater amount of GFP reconstitution. To test this hypothesis, split Firefly luciferase fused to split inteins [Schwartz E C, Saez L, Young M W, Muir T W (2007) Post-translational enzyme activation in an animal via optimized conditional protein splicing. Nat Chem Biol 3(1):50-54; Chong S, et al. (1996) Protein Splicing Involving the *Saccharomyces cerevisiae* VMA Intein. J Biol Chem 271(36):22159-22168; Selgrade D F, Lohmueller J J, Lienert F, Silver P a (2013) Protein Scaffold-Activated Protein Trans-Splicing in Mammalian Cells] were used, which relies on splicing to produce a functional luciferase protein after the two halves are brought together by Pum binding to mRNA.

Figure 20:
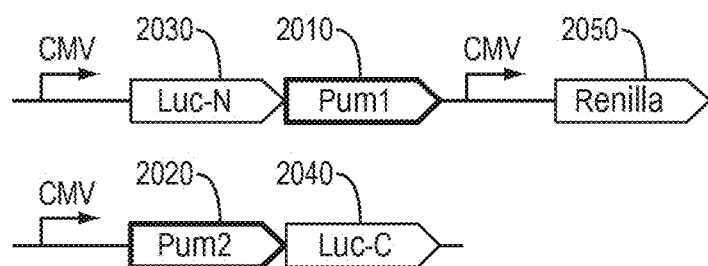

FIGS. 20-27 depict an assay for validating the ability of Pum proteins to report translation levels and the results thereof. FIG. 20 is a schematic of the reporter plasmids used. The plasmids encode for two Pum proteins 2010, 2020 that are designed to bind to various sequences within the target RNAs shown in FIG. 21, each fused to half of split Firefly luciferase 2030, 2040. One plasmid also encodes for a control gene 2050, Renilla luciferase, which helps quantify transfection efficiency and cell density.

Figure 21:
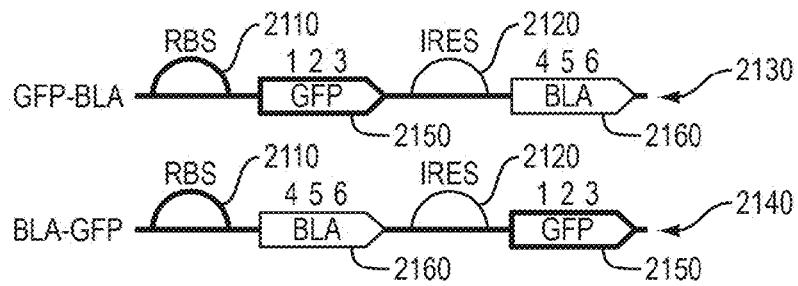

To assess translation level independently from mRNA expression level, Pum targets (8 nucleotides in length) were devised on the genes for GFP and β-lactamase (BLA). Expression of these genes was controlled by a ribosome binding site 2110 (RBS) and an internal ribosome entry site 2120 (IRES), both in that order (GFP-BLA, FIG. 21) and in the reverse order (BLA-GFP, FIG. 21). FIG. 21 depicts schematics of two different target mRNAs 2130, 2140 used to assess Pum-mediated reconstitution using the Pum vectors shown in FIG. 20. Only one of the two mRNAs is used in each experiment. The mRNAs contain sequences encoding for GFP 2150 and β-Lactamase 2160 (BLA) behind strong (ribosome binding site, RBS 2110) vs. weak (internal ribosome entry site, IRES 2120) translation start positions. They are labeled GFP-BLA 2130 and BLA-GFP 2140 for the (GFP strong, BLA weak) and (BLA strong, GFP weak) conditions, respectively. Three Pums were targeted to each of the two open reading frames, aiming for stretches of RNA with low secondary structure.

Figure 22:
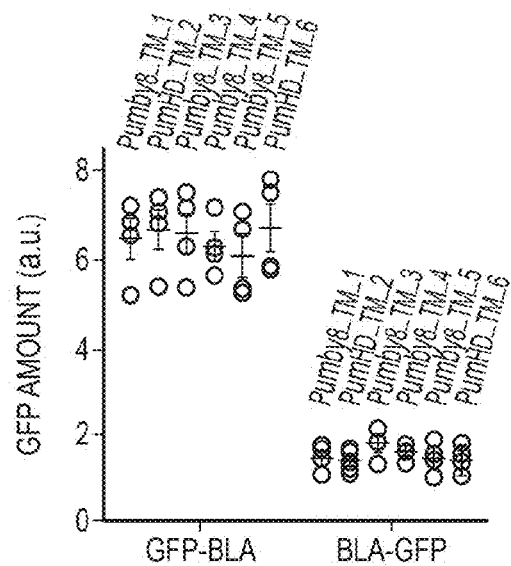
Figure 23:
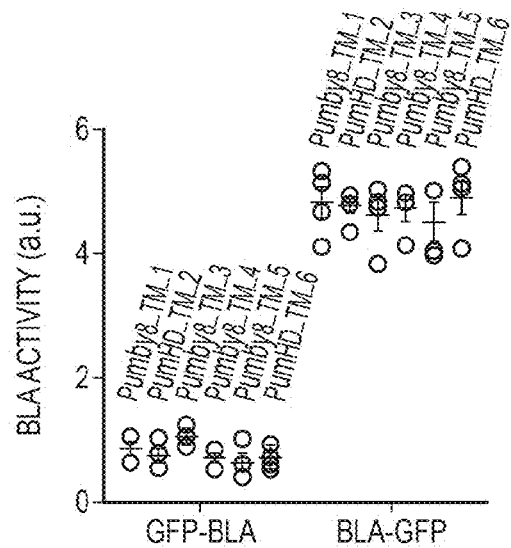

FIG. 22 depicts GFP levels (arbitrary units) measured for extracts of HEK293FT cells transfected with either GFP-BLA or BLA-GFP (as in FIG. 21, marked on the x-axis), as well as both reporter plasmids (as in FIG. 20). The label above each set of data points indicates which exact Pum site in FIG. 21 was being targeted (n=4 biological replicates). FIG. 23 reports BLA activity from the same set of biological replicates as FIG. 22. Circles represent individual data points in FIGS. 22-27; the error bars show mean±s.e.m. The amount of protein expressed by the cells was roughly 5 times higher when the corresponding gene was controlled by the RBS, compared to when it was controlled by the IRES. This was his was observed for both GFP (FIG. 22; P<0.0001) and for BLA (FIG. 23; P<0.0001). The amount of translation did not depend on whether a Pumby8 or a PumHD was targeted to the mRNA sequence (FIGS. 22 and 23; P=0.6517 and P=0.7198, respectively).

Figure 24:
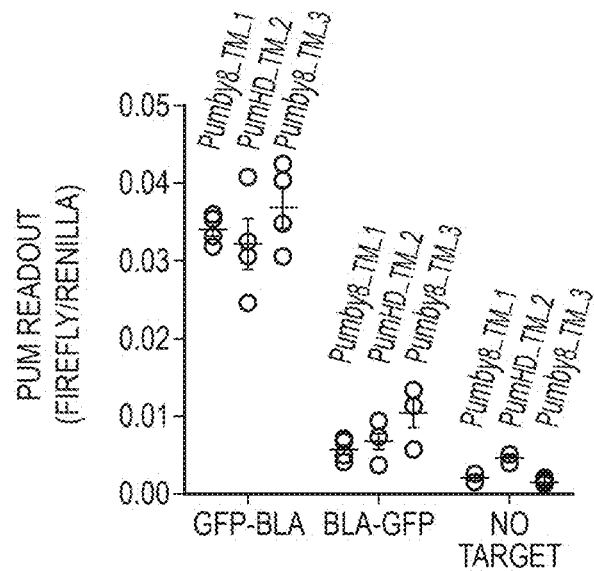
Figure 25:
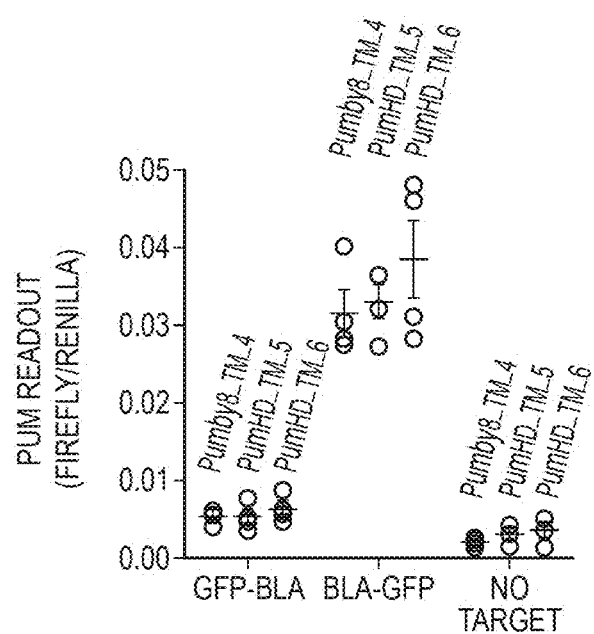

FIG. 24 is a graphical representation of firefly luciferase reconstitution (normalized to Renilla luciferase levels) mediated by Pum reassembly on RNA scaffolds, for three Pum binding sites in the GFP sequence, for cells transfected with either GFP-BLA or BLA-GFP (or no target) as well as both reporter plasmids from FIG. 20 (n=4 biological replicates for the GFP-BLA and BLA-GFP cases; n=3 biological replicates for the case of no target). FIG. 25 is a graphical representation of firefly luciferase reconstitution as in FIG. 24, but instead for Pum binding sites in the BLA sequence (n=4 biological replicates for the GFP-BLA and BLA-GFP cases; n=3 biological replicates for the case of no target). The levels of Pum-mediated luciferase reconstitution—the Pum-mediated measurement of translation used herein—were affected by whether the Pum target sequence was located behind the RBS vs. the IRES. This was observed both for Pums targeting the coding sequence of GFP (FIG. 24; P<0.0001) and Pums targeting the coding sequence of BLA (FIG. 25; P<0.0001). Pumby8 and PumHD showed indistinguishable behavior in this experiment (FIGS. 24 and 25; P=0.5261 and P=0.0854, respectively).

Figure 26:
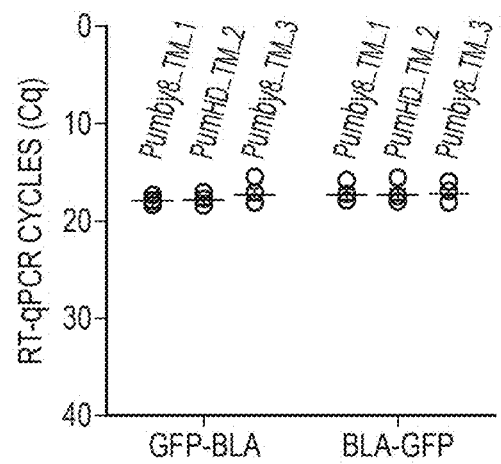
Figure 27:
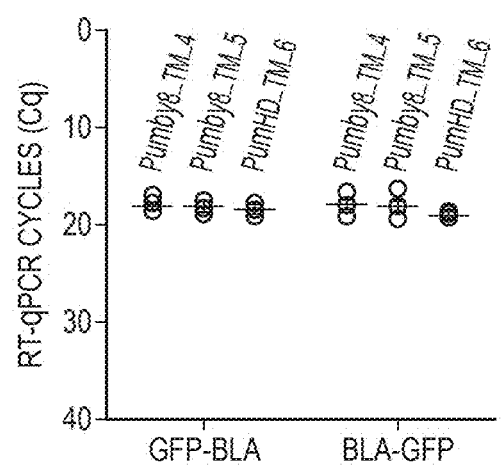

To confirm that this assay was indeed reflecting the amount of translation, and not any change in mRNA levels, reverse-transcription quantitative PCR (RT-qPCR) was used to quantitate the amount of target transcript mRNA, and it was found that the mRNA levels remained constant despite variations in protein expression (FIGS. 26 and 27; P=0.2589 and P=0.5634, respectively). FIG. 26 graphically depicts RT-qPCR measurement of the GFP transcript for the experiments of FIG. 24, where $C_q$ is the quantification cycle [Bustin S A, et al. (2009) The MIQE guidelines: minimum information for publication of quantitative real-time PCR experiments. Clin Chem 55(4):611-22] (n=4 biological replicates). FIG. 27 graphically depicts RT-qPCR measurement as in FIG. 26, but for the experiments of FIG. 25. The RT-qPCR mRNA counts for GFP were indistinguishable when Pumby8 vs. PumHD were used (FIGS. 26 and 27; P=0.6236 and P=0.1092, respectively). Thus, Pum-based reconstitution assays can be used to measure mRNA translation, independent of mRNA copy number, for various RNAs, simply by locating the mRNA target in the coding sequence of the gene.

Modular RNA Binding Protein-Based Gene Translation Facilitation.

Figure 28:
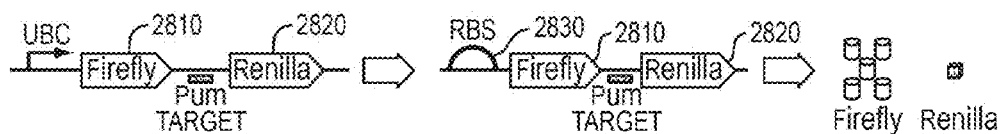
FIG. 28 is a schematic of an example reporter plasmid containing genes for Firefly and Renilla luciferases.

Another useful mRNA operation is translation initiation, previously demonstrated by fusing wild-type PumHD (or two of its mutants) to translation activation factor eIF4E [Cao J, et al. (2013) Light-inducible activation of target mRNA translation in mammalian cells. Chem Commun (Camb) 49(75):8338-40; Cao J, Arha M, Sudrik C, Schaffer D V., Kane R S (2014) Bidirectional regulation of mRNA translation in mammalian cells by using PUF domains. Angew Chemie—Int Ed 53(19):4900-4904]. The performance of Pumby in this context was assessed by simultaneously measuring the expression of two open reading frames (ORFs) from a single transcript. FIG. 28 is a schematic of a reporter plasmid containing genes for Firefly 2810 and Renilla 2820 luciferases, with the Firefly luciferase gene 2810 behind a ribosome binding site 2830 (RBS), but with the Renilla luciferase 2820 lacking such a site so that its open reading frame yields low levels of translation [Cao J, et al. (2013) Light-inducible activation of target mRNA translation in mammalian cells. Chem Commun (Camb) 49(75):8338-40].

A transcript was created that contained an RBS, a Firefly luciferase ORF, and a Renilla luciferase ORF, in that order. The RBS has a strong effect on the more proximal Firefly ORF, and a weak effect on the Renilla ORF. Between the ORFs are of one of three mRNA target sequences, present in 1, 5, or 10 copies. Table 7 contains a list of the RNA Pum target sequences for experiments of FIGS. 29 and 30. They were included 1, 5, or 10 times, along with 9, 5, or 0 "dummy" sequences AUAUAUAU, used to pad the length and keep the overall size of the mRNA constant.

TABLE 7

| Name | On-target RNA sequence | Off-target sequence |
|---|---|---|
| Pumby8_TI_2 | GAGUUGGA | UAGACUGG (Pumby8_TI_2) |
| Pumby8_TI_3 | UAGACUGG | CUCGACUG (PumHD_TI_1) |
| PumHD_TI_1 | CUCGACUG | GAGUUGGA (Pumby8_TI_1) |

Figure 29:
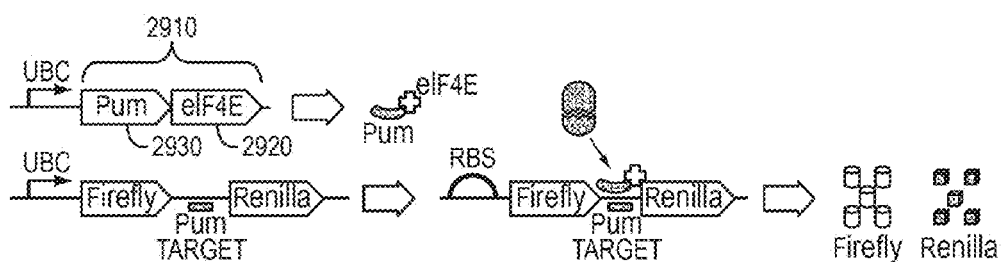
FIG. 29 is a schematic depicting how adding a driver plasmid, containing translation initiation factor eIF4E fused to a Pum protein, may be used to drive translation of an RBS-lacking open reading frame.

The target transcript was combined with various Pum-eIF4E fusion proteins to drive translation. One protein was chosen based on the PumHD architecture, PumHD_TI_1, and two based on Pumby chains, Pumby8_TI_2 and Pumby8_TI_3, all of which bind 8-nucleotide targets. FIG. 29 is a schematic depicting how adding a driver plasmid 2910, containing translation initiation factor eIF4E 2920 fused to a Pum protein 2930, may be used to drive translation of an RBS-lacking open reading frame, causing in this case the production of more Renilla luciferase.

Figure 30:
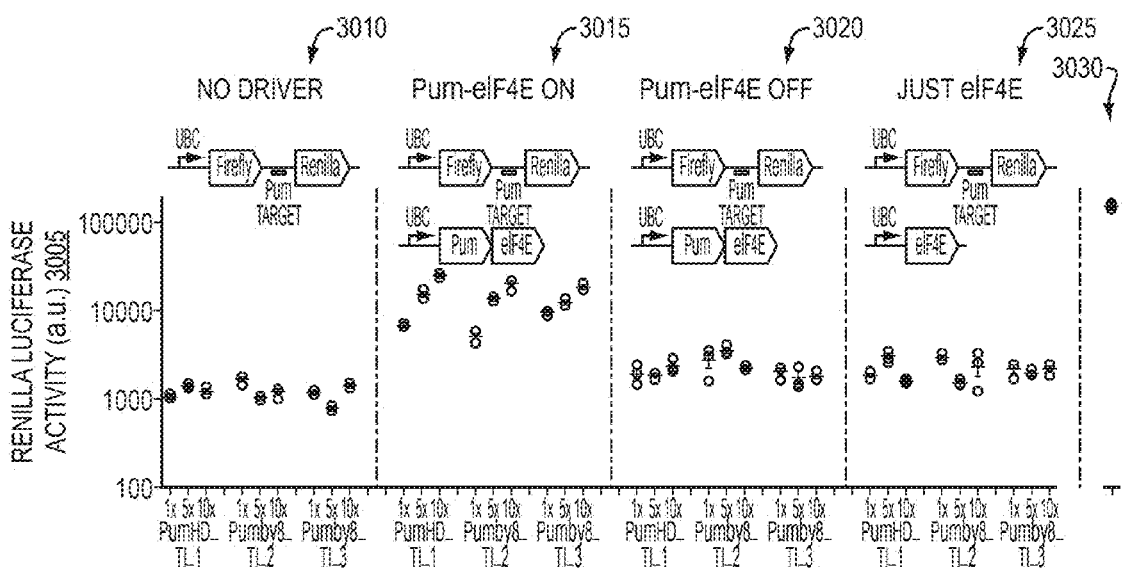
FIG. 30 depicts example results for experiments utilizing the schemes of FIGS. 28 and 29.
Figure 31:
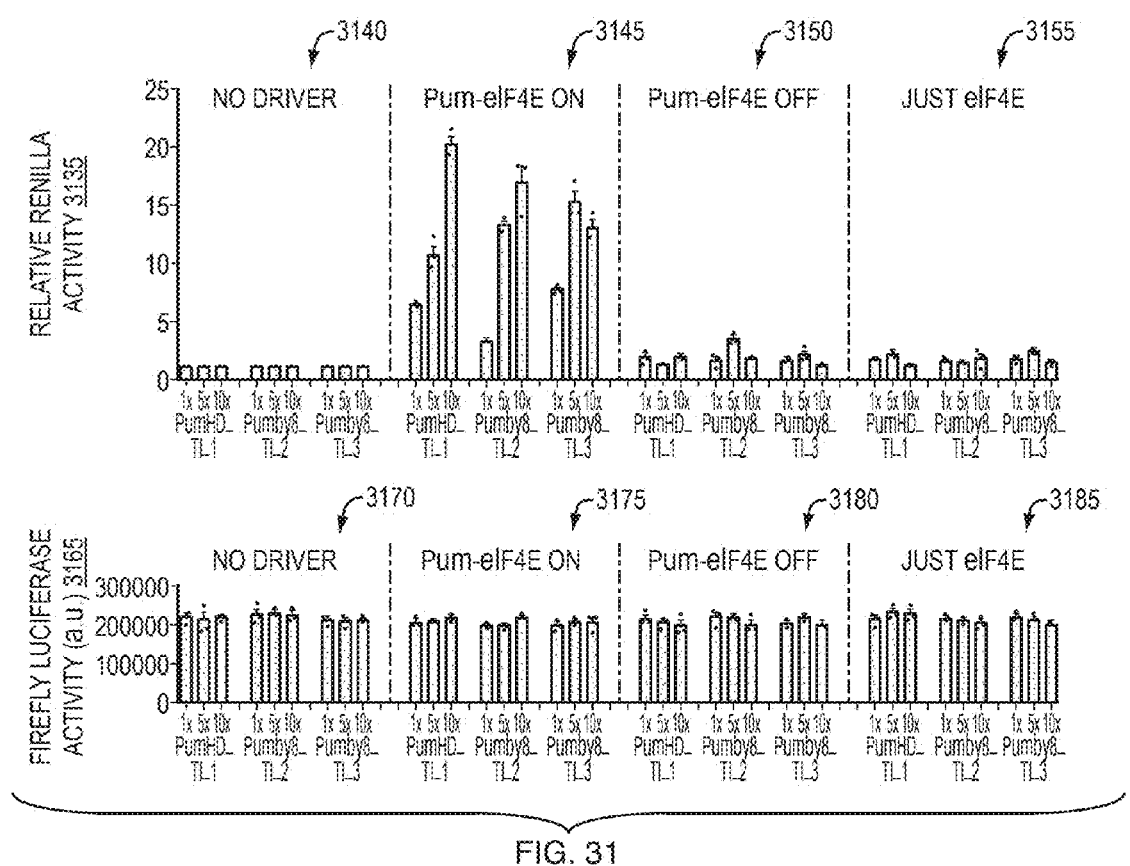
FIG. 31 depicts normalized results for the data of FIG. 30, along with results for control experiments utilizing the schemes of FIGS. 28 and 29.

FIGS. 30 and 31 depict the corresponding results for experiments utilizing the schemes of FIGS. 28 and 29. In FIG. 30, Renilla luciferase activity 3005 is reported as a measure of Pum eIF4E mediated translation initiation facilitation, using reporter plasmids bearing three different Pum target sites, in tandem repeats of 1, 5, or 10 copies in a row, in conjunction with various different driver plasmids. For a full list of the target binding sequences used in FIGS. 30 and 31, see Table 7. Pums were uniquely identified for easy reference as PumHD_TI or Pumby8 TI where TI stands for "translation initiation." Specifically shown are Renilla levels 3005 when only the reporter plasmid of FIG. 28 is used, with no driver plasmid 3010, Renilla levels 3005 when the reporter plasmid is used with an on-target driver plasmid 3015, Renilla levels 3005 when the reporter plasmid is used with an off target driver plasmid 3020, Renilla levels when the reporter plasmid is used with a driver plasmid where eIF4E is present but not fused to Pum 3025, and a control experiment 3030 with Renilla expressed directly under the UBC promoter. Shown in FIG. 31 is normalized representation 3135 of Renilla levels 3005, with Renilla level data for each variant, divided by the respective means (3140, 3145, 3150, 3155), and control firefly luciferase activity 3165 from the first open reading frame of the bicistronic luciferase vectors for the same variants (3170, 3175, 3180, 3185). Values throughout are mean±s.e.m.

It was found that, compared to baseline Renilla expression with any of the 9 target vectors on its own, expression with the correct on-target Pum-eIF4E driver increased Renilla luciferase translation by about an order of magnitude (FIG. 30 3010, 3015; P<0.0001, ANOVA with Tukey's post hoc test; normalized data presented in FIG. 31 3140, 3145). More tandem repeats led to higher boosts in expression; for example, the 10× array produced several times higher expression than the 1× (FIG. 30 3015; P=0.0002, ANOVA with Tukey's post hoc test; normalized data presented in FIG. 31 3145). In contrast, expression caused by off-target Pum proteins fused to eIF4E was no higher than baseline (FIG. 30 3020; P=0.9827, ANOVA with Tukey's post hoc test; normalized data in FIG. 31 3150), and there was no impact from eIF4E administered alone (FIG. 30 3025; P=0.9971, ANOVA with Tukey's post hoc test; normalized data in FIG. 31 3155). As a control, Firefly luciferase activity did not vary with target copy number or Pum type (FIG. 31 3170, 3175, 3180, 3185; P=0.7826). Thus, Pum proteins make it possible to up-regulate translation of proteins no need for modified translation initiation sites. It was found that Pumby8 and PumHD had the same effect as each other throughout this experiment (FIG. 30 3010, 3015, 3020, 3025: P=0.4656; FIG. 31 3170, 3175, 3180, 3185: P=0.4676).

Cell-Free Measurement of Binding Affinity of Modular RNA Binding Proteins.

FIGS. 32-37 present results from experimental cell-free measurement of binding affinity of modular RNA binding proteins according to one aspect of the invention. Throughout FIGS. 32-27, the cognate RNA is always the sequence exactly matching the whole Pum protein binding sequence, flanked as CCAGAAU*Pum_sequence*UUCG. The sequence of the bases flanking the RNA target sequence was selected from previously published studies [Abil Z, Denard C A, Zhao H (2014) Modular assembly of designer PUF proteins for specific post-transcriptional regulation of endogenous RNA. J Biol Eng 8(1):7; Ozawa T, Natori Y, Sato M, Umezawa Y (2007) Imaging dynamics of endogenous mitochondrial RNA in single living cells. Nat Methods 4(5):413-419].

Table 8 presents binding of PumHD variants and Pumby variants to cognate and noncognate RNA as measured via fluorescence anisotropy of the FAM-labeled RNA target, including a full list of the target binding sequences used in FIGS. 32-37, estimated fractions of the active protein, the calculated $K_d$ values, and standard deviations of the fits.

TABLE 8

| Protein | Active fraction | Cognate RNA | $K_a$ | STDev $K_a$ | $K_d$ nM | Noncognate RNA |
|---|---|---|---|---|---|---|
| PumHD wild-type | 0.35 | UGUAUAUA | 1.13E+10 | ± 1.71e+009 | 0.088 | ACAUAUAU |
| PumHD_KD_1 | 0.34 | GUGCUCGC | 8.50E+09 | ± 9.46e+008 | 0.118 | CACGAGCG |
| PumHD_KD_2 | 0.22 | CAUGUCAG | 2.77E+09 | ± 2.97e+008 | 0.362 | GUACAGUC |

TABLE 8-continued

| Protein | Active fraction | Cognate RNA | $K_a$ | STDev $K_a$ | $K_d$ nM | Noncognate RNA |
|---|---|---|---|---|---|---|
| Pumby8_KD_3 | 0.27 | UGUAGAUA | 7.44E+08 | ± 2.71e+008 | 1.343 | ACAUCUAU |
| Pumby8_KD_4 | 0.26 | CAUGUCAG | 2.28E+09 | ± 1.71e+009 | 0.439 | GUACAGUC |

Figure 32:
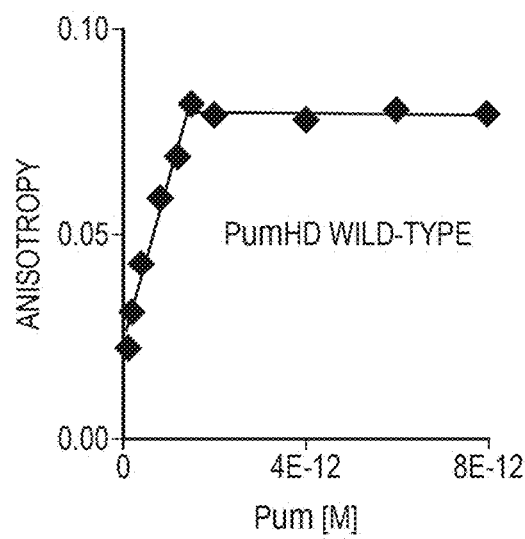
FIG. 32 presents results of a saturation experiment to estimate the active fraction of purified protein for PumHD wild-type sequence.
Figure 33:
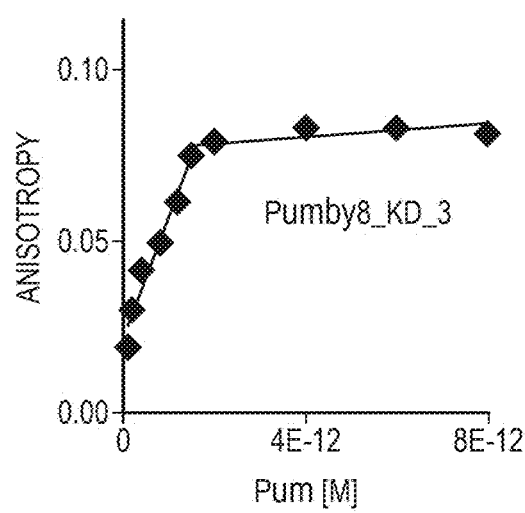
FIG. 33 presents results of a saturation experiment to estimate the active fraction of purified protein for Pumby8_KD_3.
Figure 34:
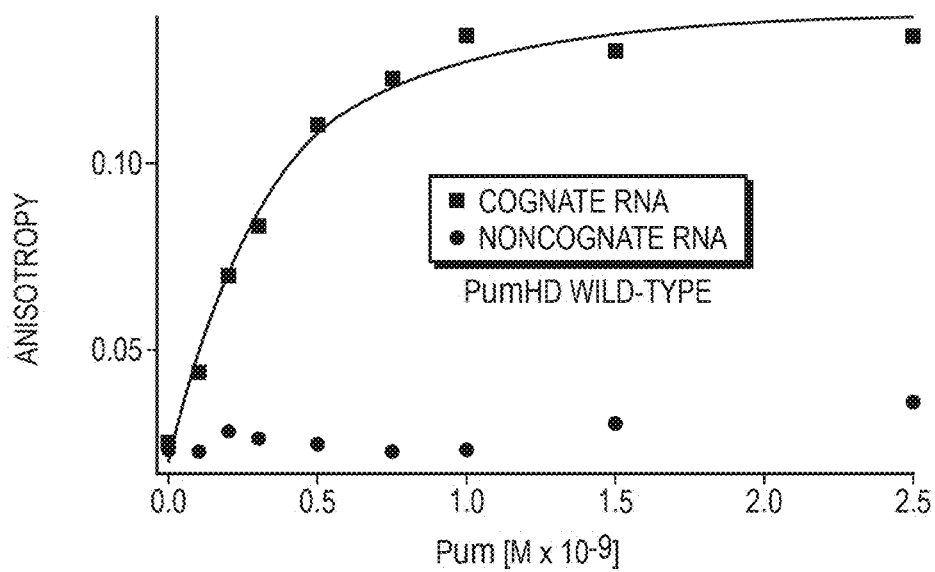
FIGS. 34-37 present $K_d$ measurement for cognate RNA and non-cognate RNA for various Pum variants: PumHD wild type sequence (FIG. 34), PumHD_KD_1 (FIG. 35), Pumby8_KD_3 (FIG. 36), and Pumby8_KD_4 (FIG. 37).
Figure 35:
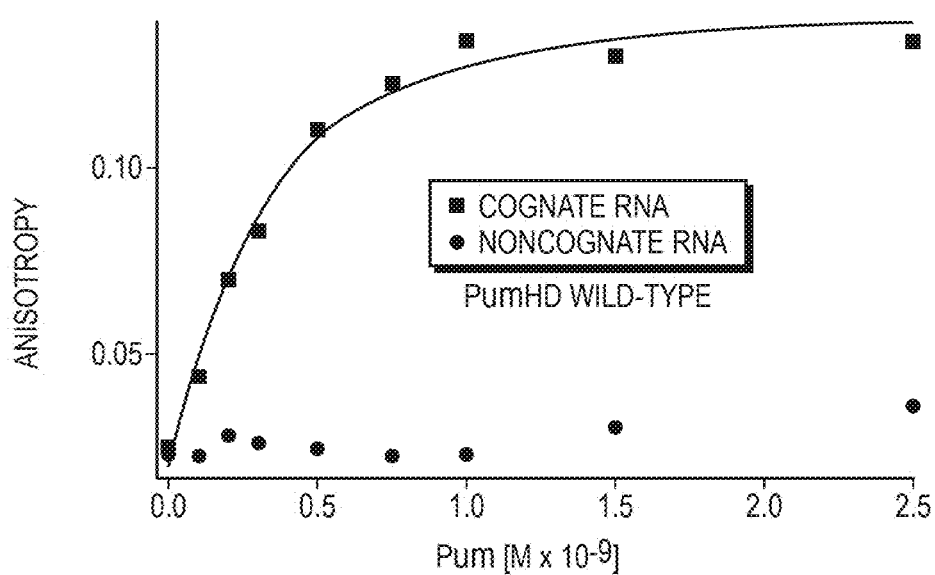
Figure 36:
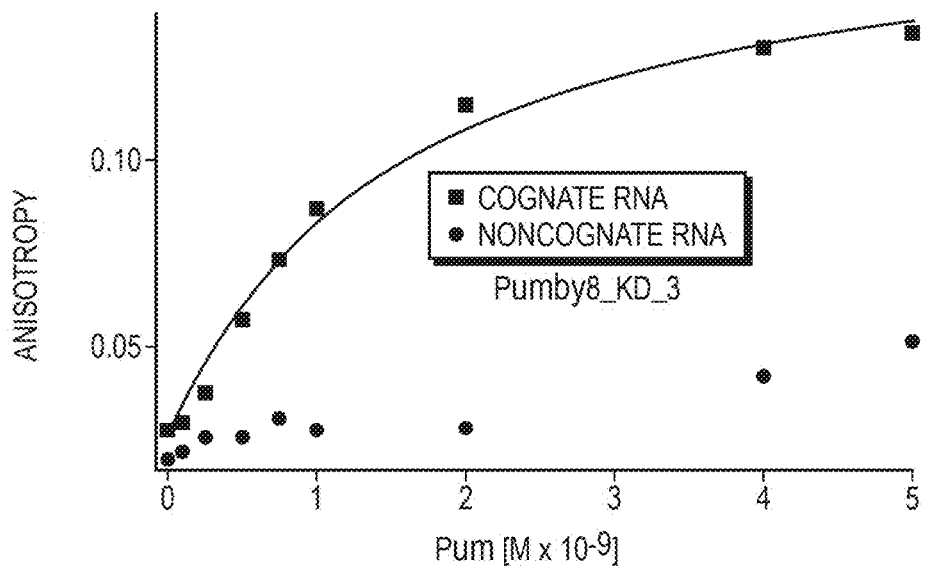

FIG. 32 presents results of a saturation experiment (Job plot) to estimate the active fraction of purified protein, for PumHD wild-type sequence. FIG. 33 presents results of a saturation experiment (Job plot) to estimate the active fraction of purified protein, for Pumby8_KD_3. Pums were uniquely identified for easy reference as PumHD_KD or Pumby8_KD, where KD refers to binding affinity.

Figure 37:
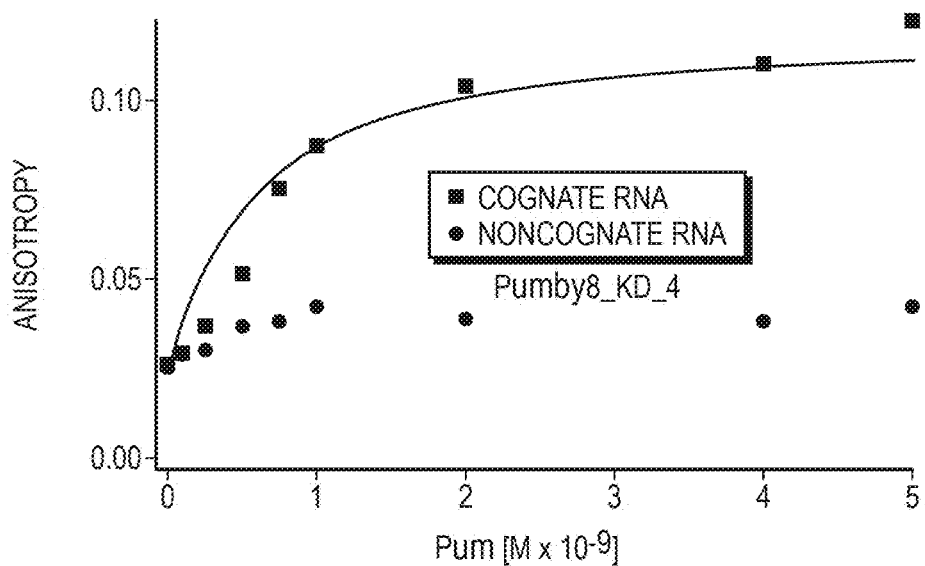

FIGS. 34-37 present $K_d$ measurement for cognate RNA (with nonlinear fit) and non-cognate RNA for various Pum variants, PumHD wild type sequence (FIG. 34), PumHD_KD_1 (FIG. 35), Pumby8_KD_3 (FIG. 36), and Pumby8_KD_4 (FIG. 37). The $K_d$ values for non-cognate RNA targets were not estimated (the attempted fits did not converge).

Orthogonality of Binding for Modular RNA-Binding Proteins.

As a further test of Pumby and PumHD, the intrinsic orthogonality between Pum proteins designed for different target sequences was validated. Specifically, seven of the Pums (all targeting 8-mer sequences) used in the experiments of FIGS. 17-27 were tested for their ability to work without crosstalk, using the luciferase reconstitution assay of FIGS. 20 and 21. Instead of using the full genes for GFP and BLA, a new set of target transcripts were created in which the required target sequences were placed at the end of the coding sequence for APEX2 peroxidase [Lam S S, et al. (2014) Directed evolution of APEX2 for electron microscopy and proximity labeling. Nat Methods 12(1):51-54], which serves as a transfection control. Table 9 contains a list of Pum proteins used for the experiments and Table 10 has a list of all landing site sequences.

TABLE 9

| Pum protein | Pum target | Fusion |
|---|---|---|
| Pumby8_TM_1A | ACGGCCAC | N-Luc |
| Pumby8_TM_1B | CAGCGUGU | C-Luc |
| PumHD_TM_2A | GAAGGCUA | N-Luc |
| Pumby8_TM_3A | GCCCGACA | N-Luc |
| Pumby8_TM_4A | CUGCUGUG | N-Luc |
| Pumby8_TM_5A | GAGCGACA | N-Luc |
| PumHD_TM_6A | GACAACAG | N-Luc |
| Pumby8_TM_8A | GACAGAUU | N-GFP |

TABLE 10

| Pums binding to the left site. Pumby8_TM_1B always binds to the right site. | Full landing site sequence Spacer1 \| Pum with N-terminal luciferase \| Spacer 2 \| Pum with C-terminal luciferase 1 Spacer 3 |
|---|---|
| Pumby8_TM_1A | AC \| ACGGCCAC \| CGUCC \| CAGCGUGU \| C (SEQ ID No. 14) |
| PumHD_TM_2A | AC \| GAAGGCUA \| CGUCC \| CAGCGUGU \| C (SEQ ID No. 15) |
| Pumby8_TM_3A | AC \| GCCCGACA \| CGUCC \| CAGCGUGU \| C (SEQ ID No. 16) |
| Pumby8_TM_4A | AC \| CUGCUGUG \| CGUCC \| CAGCGUGU \| C (SEQ ID No. 17) |
| Pumby8_TM_5A | AC \| GAGCGACA \| CGUCC \| CAGCGUGU \| C (SEQ ID No. 18) |
| PumHD_TM_6A | AC \| GACAACAG \| CGUCC \| CAGCGUGU \| C (SEQ ID No. 19) |
| Pumby8_TM_8A | AC \| GACAGATT \| CGUCC \| CAGCGUGU \| C (SEQ ID No. 20) |

The seven Pums were tested for crosstalk between each other, as measured by Firefly luciferase reconstitution normalized to Renilla luciferase expression. A series of seven target plasmids was created, each containing an APEX2 [Lam S S, et al. (2014) Directed evolution of APEX2 for electron microscopy and proximity labeling. Nat Methods 12(1):51-54] peroxidase (as a transfection control) coding sequence with a 24-bp landing site inserted immediately before the stop codon. This landing site, as for those used in FIG. 5, contains two Pum binding targets. One of the Pum binding targets was designed, across all seven landing sites, to bind Pumby8 TM 1B carrying C-terminal split Firefly luciferase (sequence CAGCGUGU), and the other binding target was designed to bind one of the seven Pums, carrying N-terminal split Firefly luciferase. The plasmids carrying the Pums are as depicted in FIG. 21.

Figure 38:
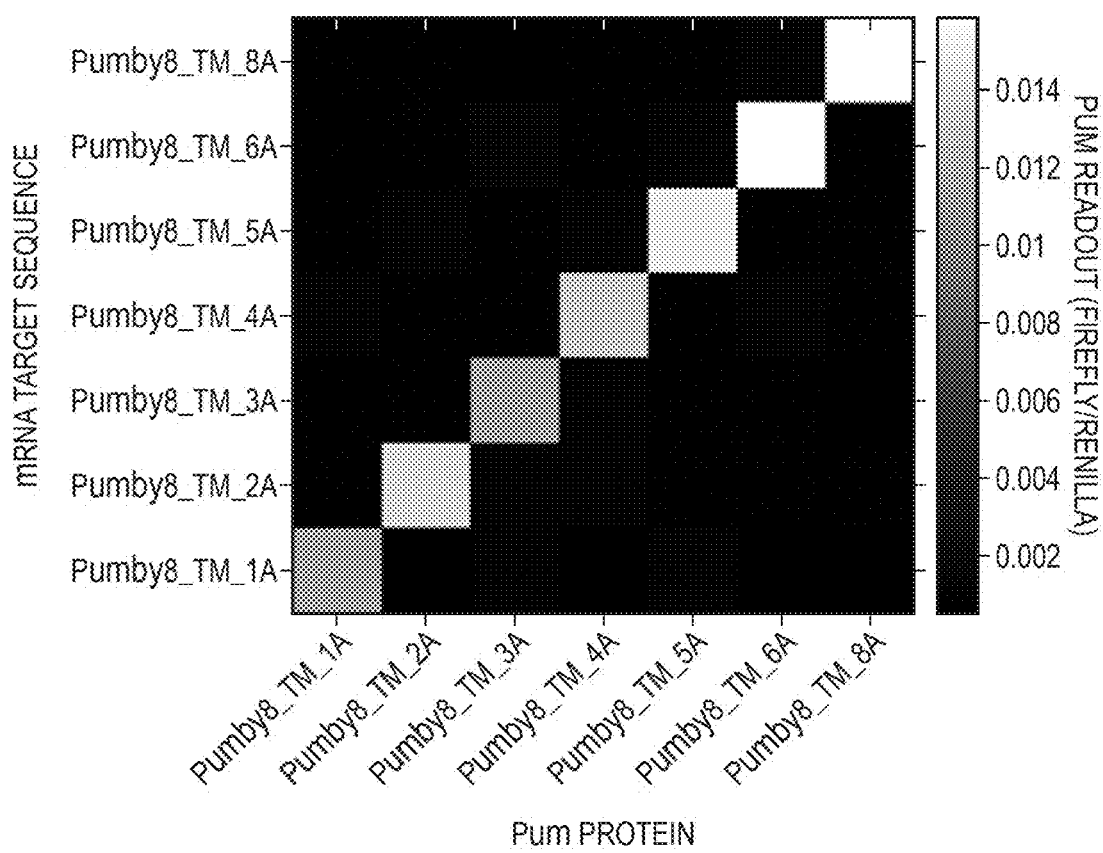
FIG. 38 presents the results of a test of seven of the Pums for crosstalk between each other, as measured by Firefly luciferase reconstitution normalized to Renilla luciferase expression.

Results are depicted in FIG. 38. The plasmid encoding for N-terminal Firefly luciferase also encodes for Renilla luciferase, which was used to normalize for cell count and transfection efficiency. Thus, the values reported in FIG. 38 have units of Firefly/Renilla luminescence (arbitrary units) and are 3 biological replicates. A match between the Pum and the landing site sequence was key for Firefly luciferase reconstitution (FIG. 38; P<0.0001). Throughout this assay, Pumby8 was indistinguishable from the PumHD equivalents (FIG. 38; P=0.0709).

The Pum proteins were also tested in an assay for gene silencing. In this assay also, there was no significant difference in mRNA silencing between Pumby8 and PumHD (P=0.8611, ANOVA with Tukey's post hoc test). Thus, through all these experiments, it was shown that PumHD and Pumby modules can enable a wide variety of protein-mediated mRNA measurements and perturbations, which can be easily performed on unmodified mRNA sequences, and, in addition, a new use of such RNA binding proteins was demonstrated, the monitoring of translation level in living cells.

In one aspect, the invention is a modular protein architecture comprising 4 protein building blocks derived from the Pumilio protein that enables universal RNA targeting, and is engineered for concatenation in chains ranging from 6 to 18 modules in length. The disclosed Pumby architecture, which uses a single repeated module to support protein generation (analogous to the TALE design), enables proteins that bind to specific RNA sequences, the measurement of mRNA expression level, imaging of mRNA dynamics, and enhancement and suppression of mRNA translation. In another aspect, the invention is a novel application of modular mRNA-binding proteins—the imaging of translation in live cells. This simple and modular technology may support, as the ability to systematically map the static distribution of RNAs in situ becomes available, the dynamic mapping and control of RNAs to assess their causal role in cellular processes such as those explored here.

A significant part of this functionality in Pumby results from its modular architecture of varying length. Longer target sequences are less likely to be found at random in the transcriptome, which helps avoid off-target effects. Furthermore, some investigations require the recognition of a long target: differentially spliced or highly repetitive transcripts, in particular, can only be uniquely identified through sequences longer than their constitutive parts. Pumby allows the creation of varying-length footprints for protection against nucleases or other RNA-binding proteins, and provides a malleable tool for tuning the energy balance of RNA secondary structure in living cells. Many engineering applications are also possible, such as assembling complex scaffolded protein-based reaction pathways in mammalian cells in an RNA-programmable fashion, as has been done before in bacteria [Delebecque C J, Lindner A B, Silver P A, Aldaye F A (2011) Organization of intracellular reactions with rationally designed RNA assemblies. Science 333(6040: 470-4].

RNA takes on complex secondary structures in live cells, and is frequently bound by endogenous RNA binding proteins. This behavior affects all technologies that rely on in vivo interactions with RNA. Pum proteins are no exception to this rule, and the use herein of several arbitrary target sequences should not be interpreted as evidence that any arbitrary Pum sequence will bind successfully, or that a Pum protein that worked in one cellular environment will work in all others. In the experiments undertaken herein, roughly ⅗ of the protein sequences tested in a new RNA context behaved as expected. With this benchmark in mind, researchers applying PumHD and Pumby to a new experiment should always validate new sequences in their final biological context.

Previous studies had probed whether PumHD variants could bind a wide diversity of NRE mutants. Here, in a single study, PumHD binding to all 4 possible nucleotides on all positions under the same set of conditions was tested. For many applications, especially if the number of bases targeted is not a key issue, or if a modular design is not required, this dataset may help with application of PumHD variants themselves to the mapping and control of RNA functions. Along these lines, other members of the Pum family have also been used to engineer selective binding between functional effector proteins and RNA targets. One of the most extensively studied is the *Caenorhabditis elegans* Fem-3 mRNA binding factor 2 (FBF-2), which is an analogue of PumHD [Campbell Z T, Valley C T, Wickens M (2014) A protein-RNA specificity code enables targeted activation of an endogenous human transcript. Nat Struct Mol Biol 21(8):732-738; Campbell Z T, et al. (2012) Cooperativity in RNA-protein interactions: global analysis of RNA binding specificity. Cell Rep 1(5):570-81; Wang Y, Opperman L, Wickens M, Hall T M T (2009) Structural basis for specific recognition of multiple mRNA targets by a PUF regulatory protein. Proc Natl Acad Sci USA 106(48):20186-91; Opperman L, Hook B, DeFino M, Bernstein D S, Wickens M (2005) A single spacer nucleotide determines the specificities of two mRNA regulatory proteins. Nat Struct Mol Biol 12(11):945-51; Bernstein D, Hook B, Hajarnavis A, Opperman L, Wickens M (2005) Binding specificity and mRNA targets of a *C. elegans* PUF protein, FBF-1. RNA 11(4):447-58]. Cooke et al. [Cooke A, Prigge A, Opperman L, Wickens M (2011) Targeted translational regulation using the PUF protein family scaffold. Proc Natl Acad Sci USA 108(38):15870-5] linked wild-type FBF-2 to the translation activator GLD2 to trigger poly(A) signal addition and up-regulate translation in *Xenopus* oocytes. Conversely, they linked the FBF-2 domain to the translational repressor CAF 1 to trigger poly(A) removal and subsequent translation down-regulation. Campbell et al. also activated translation in human U2OS cells by fusing the yeast poly(A) binding protein to an FBF-2 protein mutant that targets a specific mRNA segment of the human cyclin B1 [Campbell Z T, Valley C T, Wickens M (2014) A protein-RNA specificity code enables targeted activation of an endogenous human transcript. Nat Struct Mol Biol 21(8): 732-738]. Such architectures, if tested with every unit mutated to bind every base, or if they yield single-module building blocks, may present the kinds of utility shown here for the Pumilio protein.

The seemingly simple modular binding nature of PumHD masks a great wealth of complexity in the way that the diverse units of the protein contribute to overall protein binding. For example, it has been observed that stacking residues affect the specificity of base-binding differently at different units, that changes to the three key amino acids binding one base affect binding to neighboring bases as well as at the mutant site, and that C-terminal repeats are in general more specific than N-terminal repeats [Campbell Z T, Valley C T, Wickens M (2014) A protein-RNA specificity code enables targeted activation of an endogenous human transcript. Nat Struct Mol Biol 21(8):732-738]. PumHD variants from yeast and nematodes have been shown to bind 9-nucleobase RNA sequences even though they have only 8 protein units [Miller M T, Higgin J J, Tanaka Hall T M, Hall T M T (2008) Basis of altered RNA-binding specificity by PUF proteins revealed by crystal structures of yeast Puf4p. Nat Struct Mol Biol 15(4):397-402]. Human PumHD may bind the $5^{th}$ RNA in its target sequence using different in vivo binding modes depending on the base at that position [Lu G, Hall T M T (2011) Alternate modes of cognate RNA recognition by human PUMILIO proteins. Structure 19(3): 361-367]. Pumby presents an array in which all units have exactly the same set of modules as all the others. Thus, Pumby may present a simplified context in which to insert Pumilio modules in order to study how specific amino acids contribute to the emergent properties of modular RNA binding, independent of position-specific effects. Such future insights into the architecture of Pumilio may not only provide basic science insights into this interesting class of proteins, but help with the design of next-generation RNA binding tools.

Materials and Methods.

Golden Gate Compatible Mammalian and Bacterial Expression Vectors.

Golden Gate compatible mammalian expression vectors were prepared by eliminating BsaI sites from previously used vectors as follows. The human cytomegalovirus (CMV) major immediate-early gene enhancer/promoter expression vector, called pCI-CMV-GG, was made from the commercially available pCI vector (Promega) by removing BsaI sites from the CMV region (specifically from the (3-globin/IgG chimeric intron located downstream of the enhancer/promoter) and from the ampicillin resistance gene. The BsaI site in the chimeric intron, and thus the introduced mutation, was outside of the two known intron splice sites [Matsumoto K, Wassarman K M, Wolffe A P (1998) Nuclear history of a pre-mRNA determines the translational activity of cytoplasmic mRNA. EMBO J 17(7):2107-21]. For lower expression levels, a vector called pCI-GG-UB was created, in which the CMV promoter was replaced with the human polyubiquitin C (UBC) promoter and a single point mutation was introduced to remove the BsaI site from the UBC promoter. The efficiency of the two newly mutated promoters was confirmed by comparing the expression of the Firefly luciferase under the original promoters with that under the Golden Gate compatible mutated versions (data not shown). In both cases, the expression levels of luciferase from the original and mutated versions of the promoter were nearly identical.

Golden Gate Cloning of PumHD Variants.

Figure 39:
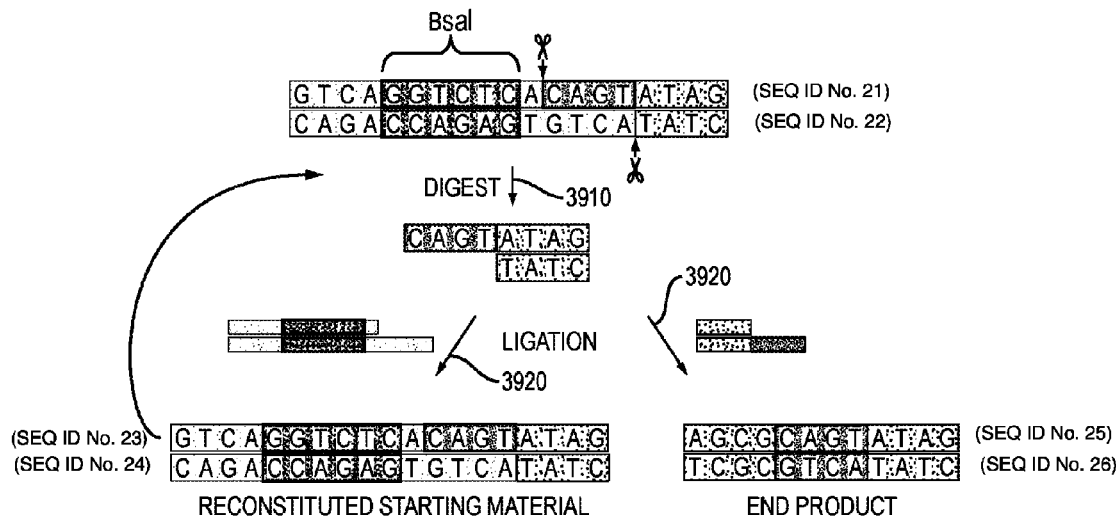
FIG. 39 depicts the rationale of the Golden Gate reaction strategy.
Figure 40:
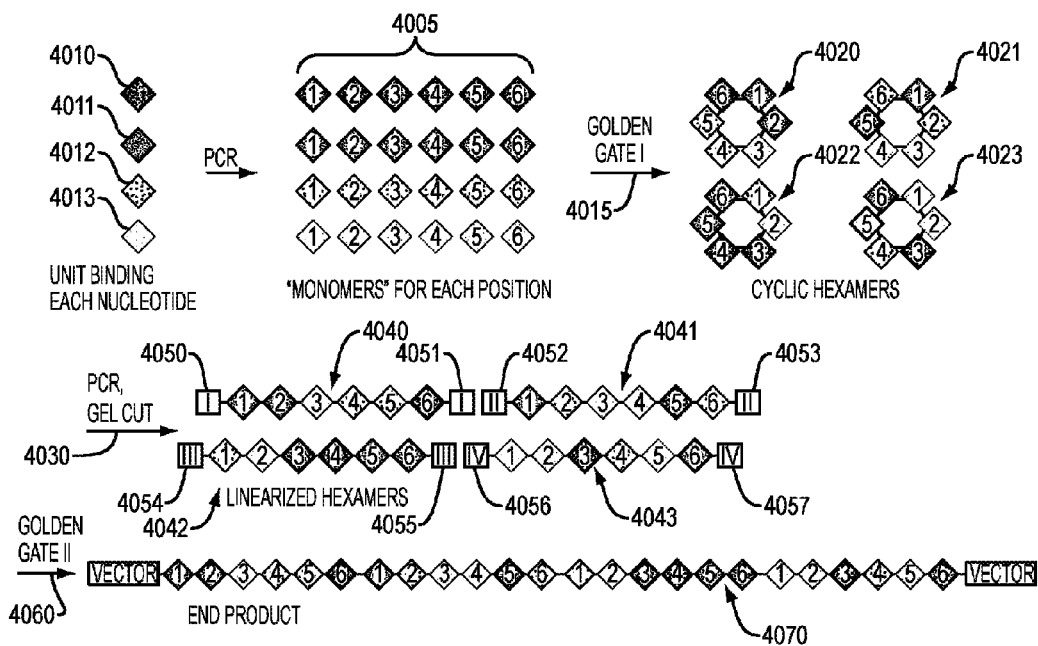
FIG. 40 depicts the specific steps of the Golden Gate reaction strategy.

The PumHD units were assembled by adapting the Golden Gate protocol from a prior TAL effector study [Sanjana N E, et al. (2012) A transcription activator-like effector toolbox for genome engineering. Nat Protoc 7(1): 171-92]. FIGS. 39 and 40 depict the general scheme of the cloning procedure. 4 base-specific variants of each of the 8 RNA-binding units in PumHD were purchased as synthetic oligonucleotides (IDT), as well as non-sequence specific units 0 and 9. The units were designed with BsmBI and BsaI restriction sites at the ends.

FIGS. 39 and 40 depict the Golden Gate reaction for PumHD and Pumby creation. FIG. 39 depicts the rationale of the Golden Gate reaction strategy. It is a two-step process of digestion 3910 with type II restriction enzymes and subsequent ligation 3920 with T7 ligase. The enzyme recognition sequence (for BsaI, 5'-GGTCTC-3') is one nucleotide removed from the cut site. The "sticky end" created after the enzyme digestion on the strand that does not contain the cut site can be ligated back with its original partner, reconstituting the original site (which can then react again), or it can be ligated into complementary "sticky end" created with the use of reversed BsaI site. The enzyme recognition site is no longer present in the latter case, resulting in a stable end product. The reaction is repeated 15-25 times (with digestion at 37° C. and ligation at 16-20° C.), driving the reaction toward product formation.

FIG. 40 depicts the specific steps. The first step in making custom Pumby and PumHD architecture assemblies is to prepare a library 4005 of "monomers" 4010, 4011, 4012, 4013 where each monomer encodes for one of the four canonical Pumby modules (FIG. 11B) or the appropriate PumHD unit (FIG. 3), as needed to bind the corresponding RNA base. Shown are 6 sets of monomers, for the Pumby case. PCR 4015 is used to add Golden Gate sites to the monomers; the overhangs determine the position that the monomers will acquire in a circular cloning intermediate 4020, 4021, 4022, 4023. These intermediates are labeled "cyclic hexamers" because they may contain up to 6 PumHD or Pumby monomers. The number of monomers that build the cloning intermediate is always 5 for PumHD (since the overall PumHD chain always contains 10 units), but varies for Pumby because it depends on the final length of the chain. Pumby6 can be built with a single cloning intermediate; Pumby8 can be made with one 5-mer intermediate and one 3-mer, or with two 4-mers; Pumby10 would take two 5-mer intermediates. The initial Golden Gate reaction assembles the monomers into a circular pentamer (for PumHD) or other n-mer (for Pumby). PCR and agarose electrophoresis purification 4030 are used to amplify circular hexamers 4020, 4021, 4022, 4023 into linear hexamers 4040, 4041, 4042, 4043 that contain the cloning overhangs 4050, 4051, 5052, 4053, 5054, 4055, 4056, 4057 for second Golden Gate reaction 4060. Second Golden Gate reaction 4060 assembles the hexamers into destination vector 4070.

A mammalian expression destination vector with point mutations in the chimeric intron of the CMV promoter and in the bLa antibiotic resistance gene to remove BsaI sites, another mammalian expression destination vector based on the pCI backbone but with the human UBC promoter, and the bacterial expression vector pBad with BsaI sites removed have all been prepared using this methodology.

To assemble the 10 units (8 RNA-binding units plus units 0 and 9) required for the PumHD architecture, two intermediate pentamer assemblies were first prepared. The Golden Gate reaction (digestion with BsmBI at 37° C. and ligation with T7 ligase at 16° C., repeated 25 times) created circular pentamers; for each PumHD assembly, one pentamer contained units 0, 1, 2, 3 and 4, and the second pentamer contained units 5, 6, 7, 8 and 9.

Any incorrect, non-circularized assemblies were digested with an ATP-dependent DNAse which acts only on linear DNA (Plasmid-Safe™ ATP-Dependent DNAse, Epicentre). The DNAse digestion reaction mixture was then used as a PCR template to amplify the linear pentamers. The PCR, performed using Herculase polymerase (Herculase II Fusion DNA Polymerases, Agilent) yielded several unspecific products ("smudged bands"), as was previously described in the case of TAL assembly. This phenomenon has been attributed to polymerases "slipping" on repetitive templates, an occurrence which can be almost entirely avoided by pre-heating the PCR reaction plus silicone oil to 98° C. and adding Herculase plus dNTPs to the hot mixture through the silicone oil. Pentamer products of the correct size were separated on a 2% agarose gel and extracted from the gel. Two linear pentamers were assembled into the final construct by the second Golden Gate reaction, using BsaI (digestion with BsaI at 37° C. and ligation with T7 ligase at 16° C., repeated 25 times) followed by a final digestion with Plasmid-Safe ATP-Dependent DNAse. The digestion mixture was used to transform Z-Competent Stbl3 *E. coli* (Zymo). Bacteria were always incubated at 30° C., as slower growth is reported to prevent scrambling of the repetitive array plasmids. The plasmids were purified using standard Miniprep kits (Zymo).

Golden Gate Cloning of Pumby.

Proteins based on the Pumby module were assembled using the general Golden Gate scheme described above (FIG. 40), with unit 6 of PumHD used on all positions in the assembly and Tyrosine as AA2 (the stacking amino acid).

One major difference with PumHD is that the total length of Pumby chains may vary; consequently, the 4 base-specific variants of each Pumby unit were prepared with cloning overhangs to circularize into n-mer cloning intermediates of whatever length was needed. Cloning intermediates with between 3 and 6 units were used to assemble final Pumby chains of up to 24 units. To create a 10-mer Pumby, for example, one hexamer and one tetramer were prepared to reach the total of 10 units in the final assembly. All bacterial amplification was done at 30° C., as above. Because of difficulty in sequencing highly repetitive arrays, for each assembly three correct clones were selected, purified and mixed (to minimize the chance of having undetected mutations because of lack of comprehensive sequencing coverage of the highly repetitive area).

Transfections and Cell Culture.

HEK293FT and HeLa cells were purchased from ATCC. All cells purchased from ATCC are tested for *Mycoplasma* contamination prior to shipping. All transfections of HEK293FT and HeLa cells were performed using Mirus X2 transfection reagent, according to the manufacturer's directions. Cells were grown in D10 medium (Dulbecco's modified Eagle medium, DMEM, supplemented with 10% v/v heat-inactivated fetal bovine serum, 100 I.U. penicillin, 100 μg/mL streptomycin and 1 mM sodium pyruvate). For imaging, cells were grown in Matrigel (Corning) coated glass 24-well plates. For qPCR, luciferase and β-Lactamase assays cells were grown in polystyrene 6-well plates (Greiner Bio-One). In all experiments, cells used were no older than passage 18, typically passage 7 to 15. All batches of cells were assigned randomly to receive one set of transfected genes or pharmacological conditions vs. another. No blinding was used.

For transfection of cells in 24-well plates, 250 ng of plasmid was transfected with 250 ng of diluent DNA (pUC19 plasmid) to keep the total amount of DNA introduced at 500 ng per well of the 24-well plate. If multiple plasmids were co-transfected, they were always in equal proportion and the total amount of plasmid DNA was always 250 ng per well of the 24-well plate (plus 250 ng of pUC19, for 500 ng of total DNA). At 24 hours post-transfection, the cell growth media was exchanged with fresh D10 to remove any remaining transfection reagent.

Targeted Transcript Silencing Via Pum-Endonuclease Fusion Protein.

Figure 41:
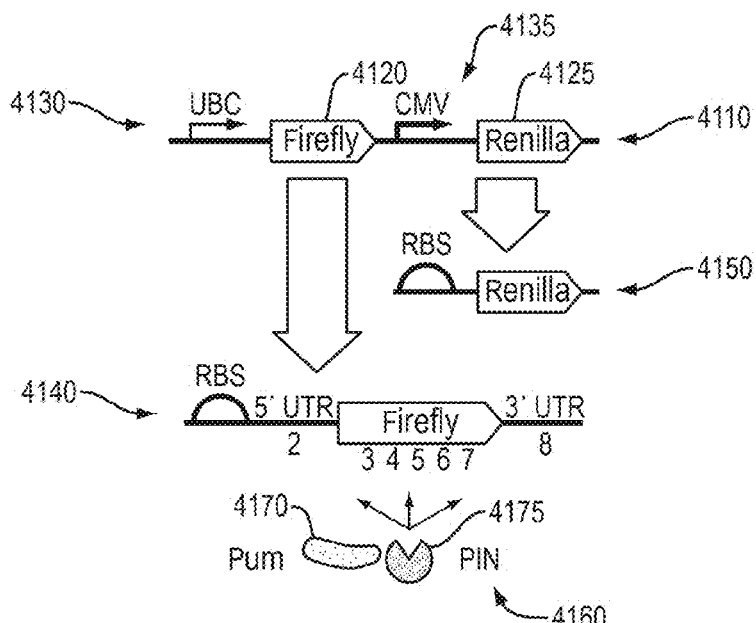
FIG. 41 is a schematic depiction of targeted transcript silencing via Pum-endonuclease fusion protein.

FIG. 41 is a schematic depiction of targeted transcript silencing via Pum-endonuclease fusion protein. As shown in FIG. 41, the RNA silencing assay uses a bicistronic target vector 4110 in which Firefly luciferase 4120 and Renilla luciferase 4125 are expressed from independent promoters 4130, 4135. This results in two separate transcripts 4140, 4150, of which only the one 4140 carrying Firefly luciferase is targeted. The Firefly mRNA is targeted by a protein fusion 4160 of Pum 4170 with the non-specific ssRNA endonuclease PIN 4175. Seven different sites on the Firefly mRNA were targeted, located before, within, and after the coding sequence. Pums were uniquely identified for easy reference as PumHD_SP or Pumby[number]_SP, where [number] represents the size of that particular Pumby and SP stands for "silencing, PIN"). Table 11 presents a list of sequences used for the experiments of FIGS. 41-45.

TABLE 11

| Target location | Name | Sequence |
|---|---|---|
| 5'UTR | PumHD_SP_1 | AGCGCCAC |
| ORF1 | Pumby8_SP_2 | CAGAAGCU |

TABLE 11-continued

| Target location | Name | Sequence |
|---|---|---|
| ORF2 | PumHD_SP_3 | CUCAGCGU |
| ORF3 | Pumby8_SP_4 | CCGGUAAG |
| ORF4 | Pumby10_SP_5 | GGGGUCGCCG (SEQ ID No. 11) |
| ORF5 | Pumby10_SP_6 | GCCGUGACUA (SEQ ID No. 12) |
| 3'UTR | Pumby10_SP_7 | GGUACCUCUA (SEQ ID No. 13) |

Figure 42:
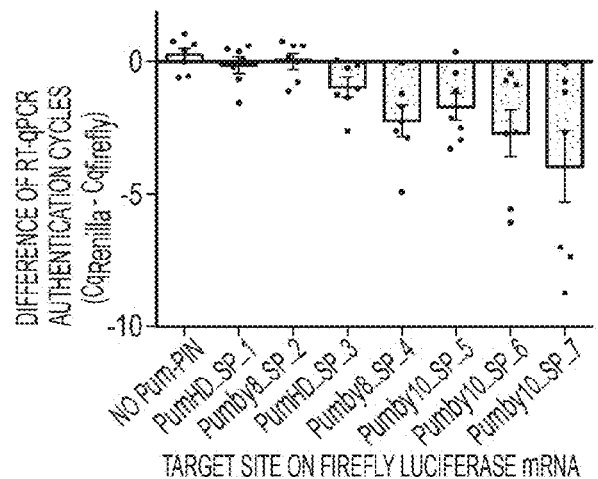
FIG. 42 is a graph of RT-qPCR measurement of Renilla vs. Firefly relative transcript levels, expressed as differences in quantification cycle ($C_q$ difference), measured from HeLa cells transfected with Pum-PIN vectors targeted to various sites on the Firefly luciferase mRNA.
Figure 43:
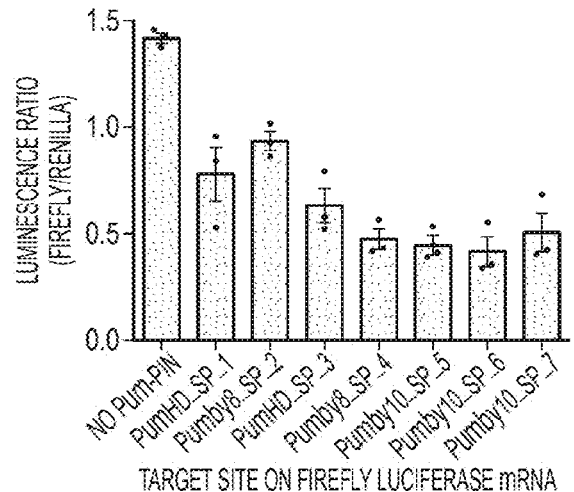
FIG. 43 is a graph of the ratio of Firefly luciferase luminescence to Renilla luciferase luminescence for HeLa cells transfected with Pum-PIN vectors targeted to the sites numbered in FIG. 41 on the Firefly luciferase mRNA.
Figure 44:
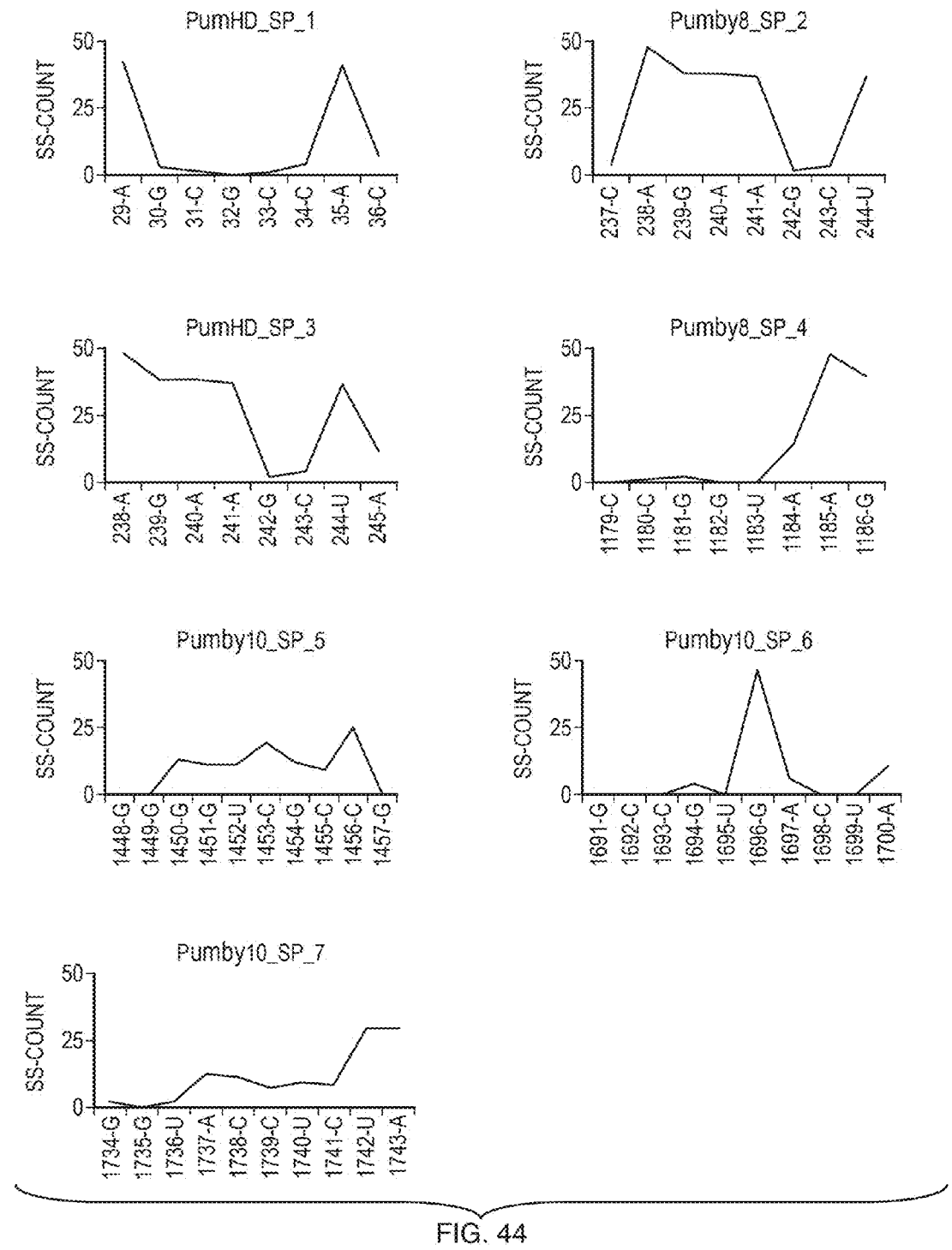
FIG. 44 provides mFold predictions of the RNA structures of those target sites.

FIG. 42 is a graph of RT-qPCR measurement of Renilla vs. Firefly relative transcript levels, expressed as differences in quantification cycle ($C_q$ difference), measured from HeLa cells transfected with Pum-PIN vectors targeted to various sites on the Firefly luciferase mRNA, as indicated by numbers in FIG. 41. Error bars are s.e.m. for 7 biological replicates and dots represent individual data points. FIG. 43 is a graph of the ratio of Firefly luciferase luminescence to Renilla luciferase luminescence for HeLa cells transfected with Pum-PIN vectors targeted to the sites numbered in FIG. 41 on the Firefly luciferase mRNA. Error bars are s.e.m. for 3 biological replicates and dots represent individual data points. FIG. 44 provides mFold predictions of the RNA structures of those target sites.

Prediction of single-stranded RNA prevalence in Pum target sites for Pum-PIN silencing.

Single-stranded RNA prevalence (ss-count), as defined by the mFold web server [Zuker M (2003) Mfold web server for nucleic acid folding and hybridization prediction. Nucleic Acids Res 31(13):3406-3415], is presented in FIG. 44 for the Pum target sequences in the luciferase plasmid in FIGS. 41-43. One hypothesis that emerges is that the Pum target sequences with the best silencing results (as observed by changes in mRNA count and luciferase activity) have a high probability of single stranded sequence near the 5' end of the RNA.

PumHD and Pumby binding in live mammalian cells measured via Pum-mediated GFP reconstitution normalized to mRuby red fluorescence (the "green red screen").

The images in FIGS. 7A-B and 12A-B were captured using cultured HEK293FT cells after a 60 hour incubation post-transfection (48 hours at 37° C. followed by 12 hours at 30° C., as has been done in previous split GFP experiments [Ozawa T, Natori Y, Sato M, Umezawa Y (2007) Imaging dynamics of endogenous mitochondrial RNA in single living cells. Nat Methods 4(5):413-419; Yamada T, Yoshimura H, Inaguma A, Ozawa T (2011) Visualization of nonengineered single mRNAs in living cells using genetically encoded fluorescent probes. Anal Chem 83(14):5708-5714]). All images for samples presented in a given figure were taken with the same light source, filter cubes and objective settings.

RNA Quantification for Translation Measurement Assays.

RNA was quantified by RT-qPCR with a LightCycler480 (Roche), using a CellsDirect One-Step qRT-PCR Kit (Life Technologies). Hydrolysis probes were designed against the sequences of EGFP, β-Lactamase, and the N-terminal fragment of split luciferase using the Custom TaqMan Assay Design Tool (Life Technologies). Life Technologies did not disclose the sequence of the probes used in this work. HEK293FT cells were grown in 24-well plates, transfected at ~70% confluence, and harvested after 24 h. For harvesting, cells were washed with DMEM (Corning), digested with 100 µl 0.05% Trypsin-EDTA (Corning) for 5 min, diluted with 800 µL PBS, and transferred to 1.5 mL microtubes. Cells were centrifuged at 200 rcf for 5 min, resuspended in 1 mL PBS, and counted with a Scepter 2.0 Handheld Cell Counter (Millipore). A given cell number for each condition depending on availability (4000 cells per condition for half of the biological replicates, 2000 cells for the other half) was extracted, centrifuged at 200 rcf for 5 min, and resuspended in PBS. The cells were then treated according to the CellsDirect protocol. Briefly, cells from each condition were mixed with lysis buffer and frozen at −80 until further use, then lysed, digested with DNAse I, and divided into RT-qPCR wells. The 20 µl reactions were carried out in 96-well plates (Roche). Each reaction included steps for reverse transcription (15 min at 50° C.) and 40 cycles of qPCR (30 s at 60° C.). Quantification cycle ($C_q$) calculations were carried out in the LightCycler480 software by the Fit Points Method (Roche). Statistical analysis of the $C_q$ values was carried out in Microsoft Excel 2011, GraphPad Prism 6 and JMP Pro 11.

For experiments in FIGS. 17-27, the data for GFP, β-Lactamase, and Pum-readout luciferase, as well as corresponding RT-qPCR data for each sample, were collected from the same biological replicates (cells grown and transfected at the same time, in adjacent wells of a microwell plate). HEK293FT cells for those experiments were harvested 72 hours post-transfection.

For the gene silencing experiments of FIGS. 41-43, the Renilla luciferase, Firefly luciferase and RT-qPCR data for each sample were collected from the same biological replicates (HeLa cells grown and transfected at the same time, in adjacent wells of a microwell plate). Cells for those experiments were harvested 48 hours post-transfection.

Orthogonality Tests.

For the orthogonality tests of FIG. 38, luciferase and APEX2 assays were performed on all technical replicates on the same day, with the same batch of reagents. APEX2 activity served as a transfection control; that is, all biological samples were screened for peroxidase activity and its presence was used as an indicator that the well had been successfully transfected with a target vector. APEX2 was chosen for this purpose because it is a modified peroxidase that shows strong activity in the mammalian cytosol and in order to provide a verifiably translated gene in which to place the landing site. The landing site needed to be within the open reading frame of a translated gene, in order for a large amount of split Firefly luciferase to be reconstituted. It was intended to exclude any samples that displayed zero peroxidase activity, but in the end, none of the samples were excluded from the study for this reason. APEX2 activity was assayed with an Amplex® Red Hydrogen Peroxide/Peroxidase Assay Kit (Invitrogen). Each biological replicate consisted of the HEK cells from one 24-well plate well, transfected with three plasmids encoding the following: Pum fused to N-terminal split Firefly luciferase, Pum fused to C-terminal split Firefly luciferase, and APEX2 fused to the landing site. All replicates were transfected with the same Pum fused to C-terminal split Firefly luciferase, so reconstitution was determined solely by the correspondence between the Pum fused to N-terminal split Firefly luciferase and its binding site. Each tile in FIG. 38 presents the average of three biological replicates.

Firefly and Renilla Luciferase Activity Assay.

The activity of Renilla luciferase and Firefly luciferase was measured using Dual-Glo luciferase Assay System (Promega) according to the manufacturer's instructions. It is to be noted that the measured luciferase activity, especially for the reconstituted split luciferase, differs significantly between experiments if the reconstituted luciferin reagent is allowed to go through more than one freeze-thaw cycle. This has been previously noted by others using a luciferase detection kit based on the same chemistry [Selgrade D F, Lohmueller J J, Lienert F, Silver P a (2013) Protein Sca ff old-Activated Protein Trans-Splicing in Mammalian Cells]. For results described herein, each "batch" of experiments (samples directly compared to each other; i.e., all biological replicates in single figure panel) was analyzed using the same, freshly prepared, batch of reagents.

For the translation quantification experiments of FIGS. 17-27, the data for GFP, β-Lactamase and Pum readout luciferase, as well as corresponding RT-qPCR data for each sample, were collected from the same biological replicates (cells grown and transfected at the same time, in adjacent wells of a microwell plate). The cell harvesting protocol for those experiments is described above in the section "RNA quantification for Translation Measurement Assays".

For gene silencing experiments of FIGS. 41-43, the Renilla luciferase, Firefly luciferase and RT-qPCR data for each sample were collected from the same biological replicates (HeLa cells grown and transfected at the same time, in adjacent wells of a microwell plate). The cell harvesting protocol for those experiments is described above in the section "RNA quantification for Translation Measurement Assays".

For the translation initiation experiments of FIGS. 29-31, cells were harvested 36 hours post-transfection by digestion with Glo Lysis Buffer (Promega), according to manufacturer's instructions.

β-Lactamase Activity Assay.

The β-Lactamase activity assays were performed using GeneBLAzer™ In Vitro Detection Kit (Invitrogen) according to the manufacturer's instructions. For the translation imaging experiments of FIGS. 17-27, the data for GFP, β-Lactamase and Pum readout luciferase, as well as corresponding RT-qPCR data for each sample, were collected from the same biological replicates (cells grown and transfected at the same time, in adjacent wells of a microwell plate). The cell harvesting protocol for those experiments is described earlier.

Quantitative GFP Assay.

The GFP activity was quantitated using GFP Quantitation Kit (BioVision) according to the manufacturer's instructions. For translation imaging experiments of FIGS. 17-27, the data for GFP, β-Lactamase and Pum readout luciferase, as well as corresponding RT-qPCR data for each sample, were collected from the same biological replicates (cells grown and transfected at the same time, in adjacent wells of a microwell plate). Thus the cell harvesting protocol for those experiments is described earlier.

Imaging of Native ATF4 Translation Via Pum-Mediated Fluorophore Reconstitution.

For the experiment described in FIGS. 18 and 19, HEK293FT cells were seeded and transfected with a pair of Pum GFP vectors and imaged as described above for the "green red screen". At 24 hours post-transfection, 0.5 µM thapsigargin was added. Cells were imaged again after 12 hours, as described above. Each experiment was performed in three biological replicates (cells grown and transfected at the same time, in adjacent wells of a microwell plate). ATF4 protein expression was quantified using an Enzyme-linked Immunosorbent Assay (ELISA) Kit for Activating Transcription Factor 4 (Cloud-Clone Corp.). The cells were harvested at indicated time points and the ELISA assays performed according to manufacturer's instructions. Each experiment was performed in three biological replicates (cells grown and transfected at the same time, in adjacent wells of a microwell plate).

Protein Expression and Purification.

A custom Golden Gate compatible bacterial expression vector was prepared, based on pBadHisB (6×His tag) vector backbone, removing BsaI site from the BLA CDS. Pum arrays were cloned into this vector as described above. His-tagged Pum variants were expressed in *E. coli* strain DH5α, grown in 100 mL RM media induced with 0.005% arabinose, at 18° C., 200 RPM, for 18 to 24 hours (until the colony reached $OD_{600}$ of 0.7). Bacterial pellets were lysed with BugBuster Protein Extraction Reagent (5 mL per 1 g of wet bacteria paste; EMD Milipore) with lysozyme (0.50 mg/mL final concentration, Thermo Scientific). The proteins were purified using Talon Spin Columns (Clontech). The purified proteins were stored in aliquots in 25% glycerol at −80° C.

Binding of Pum Variants to RNA Measured by Fluorescence Anisotropy.

Fluorescence anisotropy was used to measure the kinetics of binding of the purified Pum proteins to the cognate and non-conate RNA. The fluorescence anisotropy is widely used to investigate steady state, dynamic equilibrium binding between the protein and RNA [Shi X, Herschlag D (2009) Fluorescence polarization anisotropy to measure RNA dynamics. Methods Enzymol 469:287-302; Heyduk T, Ma Y, Tang H, Ebright R H (1996) Fluorescence anisotropy: rapid, quantitative assay for protein-DNA and protein-protein interaction. Methods Enzymol 274:492-503; Dinman J (2013) Biophysical approaches to translational control of gene expression. 317].

The cognate and non-cognate RNA targets for the purified Pum variant proteins were synthesized with 5'-labeled FAM, 6-carboxyfluorescein (IDT). The activity of the purified Pum variants was estimated with a saturation assay for each protein and its cognate RNA as described before [Abil Z, Denard C A, Zhao H (2014) Modular assembly of designer PUF proteins for specific post-transcriptional regulation of endogenous RNA. J Biol Eng 8(1):7]. 50 nM cognate RNA was mixed with increasing concentration of the protein (measured by NanoDrop, Thermo Scientific) in the binding buffer (25 mM Tris-HCl pH 7.5, 0.5 mM EDTA, 50 mM KCl, 0.1 mg/mL BSA). The 100 μL samples were assayed, in duplicates, for fluorescence anisotropy using a Cary Eclipse fluorimeter (Varian) with Manual Polarizer Accessory (Varian). The cognate RNA is always the sequence exactly matching the whole Pum protein binding sequence, flanked as CCAGAAU*Pum_sequence*UUCG (for full list of sequences, see Table 8) with flanking bases selected according to previously published studies [Abil Z, Denard C A, Zhao H (2014) Modular assembly of designer PUF proteins for specific post-transcriptional regulation of endogenous RNA. J Biol Eng 8(1):7; Ozawa T, Natori Y, Sato M, Umezawa Y (2007) Imaging dynamics of endogenous mitochondrial RNA in single living cells. Nat Methods 4(5):413-419]. Fluorescence anisotropy was calculated as a unitless ratio defined as $R=(I_=-I_\perp)/(I_=+2I_\perp)$, where I is the emission intensity parallel ($I_=$) or perpendicular ($I_\perp$) to the direction of polarization of the excitation source. The stoichiometric point of each saturation plot was used to estimate the active protein fraction (See FIGS. 32-37 for example plots). The $K_d$ of each protein to its cognate and non-cognate RNA was subsequently measured, using the protein concentration corrected to the active protein fraction, with constant concentration of RNA. The $K_d$ was calculated from a non-linear fit in IgorPro 6.22 of the anisotropy vs. protein concentration plot to the equation [Qu X, Chaires J B (2000) Analysis of drug-DNA binding data. Methods Enzymol 321:353-69]:

$$F([\text{protein}])=(((((([\text{protein}]*K_a+[\text{RNA}]*K_a+1)-(([\text{protein}]*K_a+[\text{RNA}]*K_a+1)^2-4*K_a^2*[\text{RNA}]*[\text{protein}])^{0.5}))/(2*K_a))*(F_b-F_0)/[\text{protein}])+F_0)$$

where [protein] is the concentration of the active fraction of the protein and [RNA] is the RNA concentration. Example anisotropy measurement plots are shown in FIGS. 32-37 and the $K_d$ values for binding of PumHD variants and Pumby to cognate and non-cognate RNA are shown in Table 8.

Stability of Pum Variants Measured by a Thermal Shift Assay.

The $T_m$ of purified PumHD and Pumby variants was measured using a thermal shift assay with SYPRO Orange (Invitrogen) dye according to the previously described protocol. Briefly, the 2.5 μM peptide samples were prepared in 100 mM HEPES (pH=7.4), 150 mM NaCl and 5×SYPRO Orange dye. Fluorescence vs temperature was measured with a LightCycler480 (Roche) with a ramp rate of 1.2° C./min. The melting temperature was obtained as a midpoint of the thermal unfolding curve by fitting the slope of the curve to the sigmoid equation in Igor Pro 6.37:

$$F=\text{base}+(\max/(1+\exp((Tm-x)/(\text{rate}))))$$

The reported $T_m$ is an arithmetic average of 4 replicates; Tm obtained from all independent replicates was within 1° C. from the reported average value.

Figure 45:
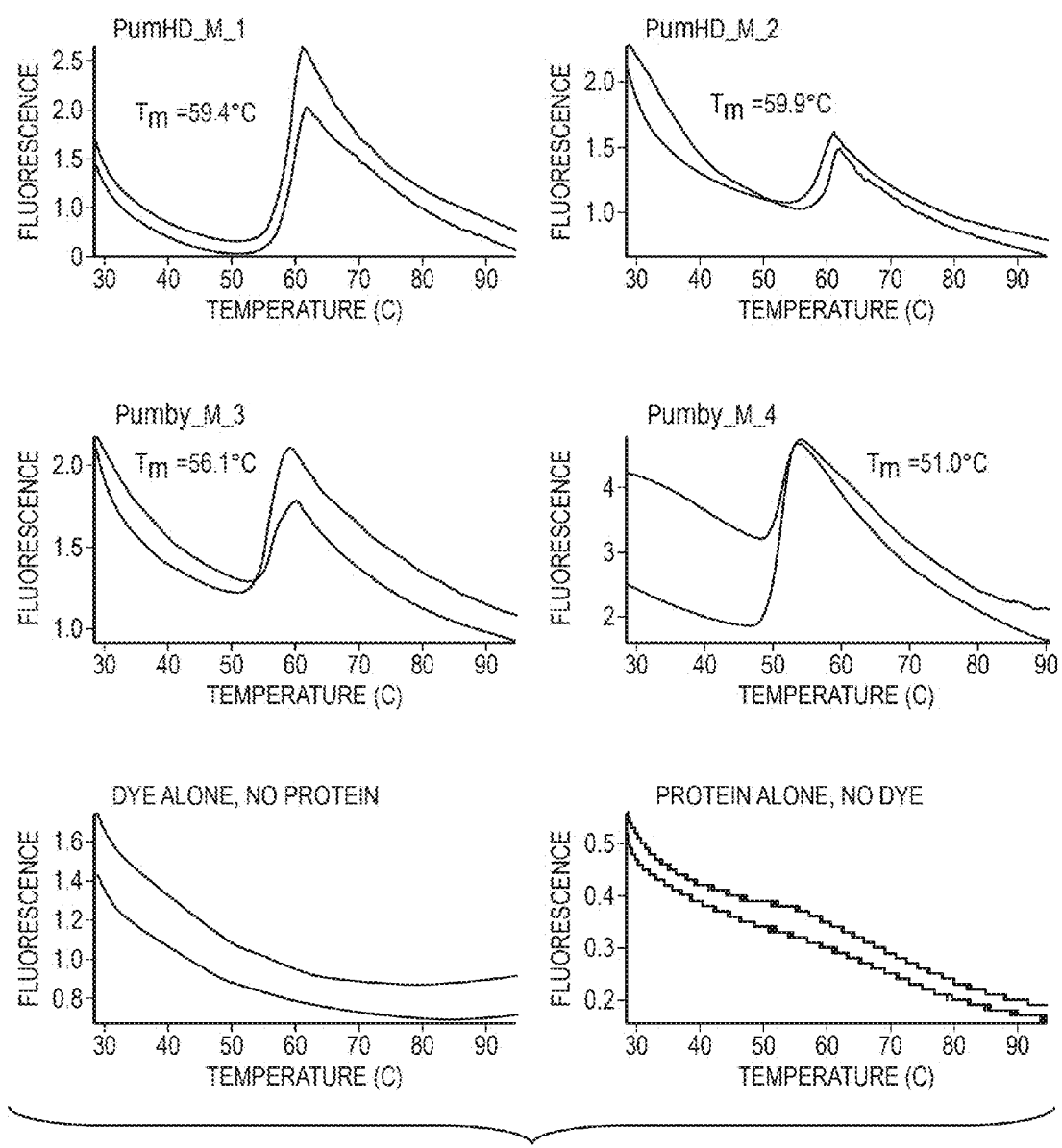
FIG. 45 presents melting plots and $T_m$ results for Pum variants measured via a thermal shift assay.

Stability of Pum variants measured via a thermal shift assay. FIG. 45 presents melting plots and $T_m$ results for Pum variants measured via a thermal shift assay. Each plot shows two representative melt graphs for each protein. The list of protein sequences is found in Table 12.

TABLE 12

| Name | Pum protein sequence |
|---|---|
| PumHD_M_1 | AUAUAUGU |
| PumHD_M_2 | CGUGUGAC |
| Pumby_M_3 | AUAUAUGU |
| Pumby_M_4 | CGUGUGAC |

The reasoning behind the sample sizes was not based upon a power analysis, since this work was directed to creating a new technology. It was therefore attempted to validate the tool by trying many different biological validations, in different contexts, in order to understand the biological impact of the tool in the context of different questions. Each experiment was repeated on a minimum of nine technical replicates.

General Assembly of Custom Pum Repeats.

The cloning of proteins like Pumilio, with highly repetitive structures, is challenging. Recent studies have presented assembly methods for Pumilio proteins based on the wild-type architecture, based on single-step Golden Gate cloning procedures [Abil Z, Denard C A, Zhao H (2014) Modular assembly of designer PUF proteins for specific post-transcriptional regulation of endogenous RNA. J Biol Eng 8(1):7]. A two-step Golden Gate cloning protocol previously developed for TAL effectors [Sanjana N E, et al. (2012) A transcription activator-like effector toolbox for genome engineering. Nat Protoc 7(1):171-92] was modified for use in this technology. The protocol described permits the efficient construction of assemblies with variable length and sequence.

At the beginning of the cloning procedure, a library of "monomers" with Golden Gate cloning overhangs is prepared, where each monomer is the sequence for a Pumilio unit (FIG. 40). For PumHD architecture assembly, that library is comprised of 8 different units in 4 versions each: every unit of PumHD architecture in a variant that binds to each of the 4 canonical RNA bases. For Pumby, the library contains the four versions of one screened and optimized binding unit. These libraries can be used to construct PumHD or Pumby chains of any sequence. Each of the monomers is prepared in one of 5 (for the PumHD architecture) or in one of 6 (e.g., for the 6-mer, 12-mer, and 18-mer Pumby) variants, with GoldenGate cloning overhangs placing it in the correct position of circular cloning intermediate composed of 5 (for PumHD architecture) or 6 (for 6-mer, 12-mer, and 18-mer Pumby) Pum units. To prepare custom assemblies, in the first Golden Gate reaction circular cloning intermediate pentamers (for PumHD architecture) or hexamers (for 6-mer, 12-mer, or 18-mer Pumby chains) of Pum units are prepared. For Pumby chains that are not a multiple of 6, one can of course combine different sets of building blocks, e.g. a 6-mer and a 4-mer can be combined to make a 10-mer. Those circular n-mers are subsequently linearized to produce linear cloning intermediates. The linear intermediates are then assembled into the destination vector in the second Golden Gate reaction. For each PumHD chain, two pentamers were assembled into the final vector (total of 10 units: 8 RNA-binding units plus non-binding units 0 and 9). For this work, several destination vectors compatible with Golden Gate reactions have been created. These vectors contain point mutations to remove BsaI enzyme sites from the CMV and UBC promoters, from the pCI vector backbone, and from the βLa antibiotic resistance gene.

Sequence of Pum Targeting Gene of Interest for Quantification of Translational Activity.

mRNA in live cells has complex folding that is often not well understood [Kertesz M, et al. (2010) Genome-wide measurement of RNA secondary structure in yeast. Nature 467(7311):103-7; Shabalina S A, Ogurtsov A Y, Spiridonov N A (2006) A periodic pattern of mRNA secondary structure created by the genetic code. Nucleic Acids Res 34(8):2428-37]. As with all technologies targeting RNA in live cells, it is advised to utilized multiple Pum targeting sequences to validate a lack of nonspecific binding or a lack of secondary structure that prevents binding to the targeted region of interest. In the case of imaging translation, in addition to the sequences reported in Table 6, three additional pairs of sequences targeting the GFP gene and two targeting the BLA gene were tested. Either no measureable Pum-mediated split luciferase reconstitution was observed (suggesting that Pum binding to the target mRNA does not happen, presumably due to the secondary structure of the mRNA region), or split luciferase reconstitution not corresponding to the translation activity of the gene was observed (suggesting the Pum binding accidentally targets native, constitutively expressed genes). Those sequences can be found in Table 13, which presents a list of non-specific and incorrect binding of Pum sequences to the GFP and BLA genes.

TABLE 13

| Label | Sequences (Pum1, Pum2) |
|---|---|
| Pumby8_TM_10 | GAAACACU, AGGUGAAG |
| Pumby8_TM_11 | GGAACCGG, AGCCGAAA |
| Pumby8_TM_12 | GCUGACCC, UUCAUCUG |
| PumHD_TM_13 | AGGGCAUC, CAAGGAGG |
| Pumby8_TM_14 | GGAUCACU, CAUGGACG |

Promiscuity of Pum Unit 4.

It has been previously suggested that unit 4 of PumHD does not distinguish between U, A, or C nucleotides. This was investigated by measuring the $K_d$ of binding to the target, with the nucleotide binding Pum unit 4 mutated to each of the 4 possible bases (A, U, C and G). Indeed, the $K_d$ of unit 4 binding to A, U and C is similar, whereas introducing G on this position in the RNA template causes a significant decrease in binding affinity.

Pum-Mediated mRNA Silencing.

A general endonuclease PIN domain has been previously fused with wild type PumHD and 5 different Pum mutants, creating a sequence-specific nuclease that works well in cultured cells [Choudhury R, Tsai Y S, Dominguez D, Wang Y, Wang Z (2012) Engineering RNA endonucleases with customized sequence specificities. Nat Commun 3:1147]. In this experiment, it is demonstrated that Pumby can be fused to the PIN domain to direct nuclease activity towards transcripts in cultured cells. Both the PumHD architecture and Pumby chains were used to create series of Pum-PIN constructs targeting different areas of the Firefly luciferase gene. Several PumHD architecture and Pumby variants were tested, showing silencing of the luciferase in response to the Pum-mediated nuclease activity (FIGS. 41-43). A bicistronic reporter vector containing Firefly luciferase (the gene targeted for silencing) and Renilla luciferase (used as a control for cell density, transfection efficiency and non-specific nuclease activity) was prepared. This double luciferase vector was co-expressed with the vector containing Pum-PIN constructs (where Pum is either PumHD architecture-based or Pumby module-based, binding different RNA recognition sequences within the Firefly luciferase gene; see Table 11 for all sequences used). A control ("No Pum-PIN") was prepared, where the Pum-PIN was left out and only the reporter plasmid was present, with PumHD protein not targeting any sequence of the luciferase vector (FIG. 41). It has been previously shown that PIN domain alone, without an RNA binding protein fused to it, does not exhibit gene silencing activity. Therefore, the RNA binding protein domain is necessary to localize the PIN nuclease domain to a target [Choudhury R, Tsai Y S, Dominguez D, Wang Y, Wang Z (2012) Engineering RNA endonucleases with customized sequence specificities. Nat Commun 3:1147].

In each experiment, HeLa cells were co-transfected with one of the Pum-PIN vectors (where Pum was either PumHD or Pumby) with the double luciferase vector. A decreased copy number of the Firefly luciferase mRNA relative to the Renilla luciferase mRNA was observed, as measured by RT qPCR experiments (FIG. 42; P=0.0003 for factor Turn Target Site'; one-way ANOVA), as well as decreased Firefly luminescence relative to Renilla (Fig. S2C; P<0.0001 for factor 'Pum Target Site'; one-way ANOVA). For some of the Pum target sites, the difference in RT-qPCR cycles equated to a reduction of Firefly vs. Renilla by 2-4 cycles, with the corresponding protein reduction of around 70%. It is worth noting that, as it is the case with siRNA and all other techniques relying on binding of a tool to a gene (RNA or DNA) in live cells, there is the potential for non-specific interactions caused by binding of the tool to sequences similar to the target sequence. Also, secondary structure formation on the mRNA of the targeted gene can prevent efficient binding to that region. Therefore, it is necessary to test several candidate sequences targeting different areas of the gene of interest, as with all RNA-binding tools.

While preferred embodiments of the invention are disclosed herein and in the attached materials, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention.

What is claimed is:

1. A modular protein architecture for RNA binding, comprising a set of six-residue peptide modular units concatenated together to form a chain of six or more six-residue peptide modular units,
   wherein each six-residue peptide modular unit consists of an amino sequence from the RNA-binding protein Pumilio Homology Domain or the Pumby protein,
   wherein the residues of the six-residue peptide modular unit are defined in one of the thirty-two amino acid sequences in FIG. 3 at amino acid positions 1, 2 and 5,
   wherein each six-residue peptide modular unit, when concatenated together to form a chain of six or more six-residue peptide modular units, has a preferred affinity for a specific target RNA base,
   wherein the chains of six-residue peptide modular units provide the ability to bind arbitrary RNA sequences, with high specificity and fidelity, by varying the sequence of the six-residue peptide modular units within the chains, and
   wherein the amino acids in positions 1 and 5 of each six-residue peptide modular unit provide the preferred affinity of the six-residue peptide modular unit for the specific RNA base and the amino acid at position 2 of each six-residue peptide modular unit serves as a stacking unit between concatenated six-residue peptide modular units.

2. The modular protein architecture for RNA binding of claim 1, wherein the protein modules have four canonic forms, with each canonic form having a preferred affinity for a different RNA base.

3. The modular protein architecture for RNA binding of claim 2, wherein the four canonic forms are characterized by the RNA base with which they have a preferred affinity, the two amino acids of the six-residue peptide modular unit that provide the preferred affinity for that base, and the amino acid of the six-residue peptide modular unit that serves as a stacking unit between concatenated six-residue peptide modular units.

4. The modular protein architecture for RNA binding of claim 3, the four canonic forms consisting of:
   Form 1, which has a preferred affinity for RNA base Adenine, and has Cysteine at position 1, Tyrosine at position 2, and Glutamine at position 5;
   Form 2, which has a preferred affinity for RNA base Uracil, and has Asparagine at position 1, Tyrosine at position 2, and Glutamine at position 5;
   Form 3, which has a preferred affinity for RNA base Guanine, and has Serine at position 1, Tyrosine at position 2, and Glutamic Acid at position 5; and
   Form 4, which has a preferred affinity for RNA base Cytosine, and has Serine at position 1, Tyrosine at position 2, and Arginine at position 5.

5. The modular protein architecture for RNA binding of claim 1, wherein the concatenated six-residue peptide modular units form 8-mers from the Pumilio Homology Domain.

6. The modular protein architecture for RNA binding of claim 4, wherein the concatenated six-residue peptide modular units form 8-mers from the Pumilio Homology Domain.

7. The modular protein architecture for RNA binding of claim 1, wherein the stacking unit at position 2 is Tyrosine or Arginine.

8. A universal programmable RNA-binding protein comprising a six-residue peptide modular unit,
   wherein the six-residue peptide modular unit can be concatenated together to form a chain of six or more six-residue peptide modular units,
   wherein the six-residue peptide modular unit consists of an amino sequence from the RNA-binding protein Pumilio Homology Domain or the Pumby protein,
   wherein the residues of the six-residue peptide modular unit are defined in one of the thirty-two amino acid sequences in FIG. 3 at amino acid positions 1, 2 and 5,
   wherein the six-residue peptide modular unit, when concatenated together to form a chain of six or more six-residue peptide modular units, has a preferred affinity for a specific target RNA base,
   wherein the concatenated chains of six-residue peptide modular units provide the ability to bind arbitrary RNA sequences, with high specificity and fidelity, by varying the sequence of the six-residue peptide modular units within the chains, and
   wherein the amino acids in positions 1 and 5 of each six-residue peptide modular unit provide the preferred affinity of the six-residue peptide modular unit for the specific RNA base and the amino acid at position 2 of each six-residue peptide modular unit serves as a stacking unit between concatenated six-residue peptide modular units.

9. The universal programmable RNA-binding protein of claim 8, wherein the modular unit has a preferred affinity for RNA base Adenine, modular unit amino acid 1 is Cysteine, modular unit amino acid 2 is Tyrosine, and modular unit amino acid 5 is Glutamine.

10. The universal programmable RNA-binding protein of claim 8, wherein the modular unit has a preferred affinity for RNA base Uracil, modular unit amino acid 1 is Asparagine, modular unit amino acid 2 is Tyrosine, and modular unit amino acid 5 is Glutamine.

11. The universal programmable RNA-binding protein of claim 8, wherein the modular unit has a preferred affinity for RNA base Guanine, modular unit amino acid 1 is Serine, modular unit amino acid 2 is Tyrosine, and modular unit amino acid 5 is Glutamic Acid.

12. The universal programmable RNA-binding protein of claim 8, wherein the modular unit has a preferred affinity for RNA base Cytosine, modular unit amino acid 1 is Serine, modular unit amino acid 2 is Tyrosine, and modular unit amino acid 5 is Arginine.

13. The universal programmable RNA-binding protein of claim 8, wherein a plurality of the modular units are concatenated to form an 8-mer from the Pumilio Homology Domain.

14. A set of six-residue peptide modular units concatenated together to form a chain of six or more six-residue peptide modular units, wherein each of the six-residue peptide modular units are according to claim 8, wherein at least one of the six-residue peptide modular units has a preferred affinity for RNA base Adenine and wherein at least one of the six-residue peptide modular units has a preferred affinity for RNA base Cysteine and wherein at least one of the six-residue peptide modular units has a preferred affinity for RNA base Guanine and wherein at least one of the six-residue peptide modular units has a preferred affinity for RNA base Uracil.

15. A method for binding an RNA molecule of arbitrary sequence length and composition, the method comprising the steps of:
producing a modular protein architecture for RNA binding of comprising a set of six-residue peptide modular units concatenated together to form a chain of six or more six-residue peptide modular units,
wherein each six-residue peptide modular unit consists of an amino sequence from the RNA-binding protein Pumilio Homology Domain or the Pumby protein,
wherein the residues of the six-residue peptide modular unit are defined in one of the thirty-two amino acid sequences in FIG. 3 at amino acid positions 1, 2 and 5,
wherein each six-residue peptide modular unit, when concatenated together to form a chain of six or more six-residue peptide modular units, has a preferred affinity for a specific target RNA base,
wherein the concatenated chains of six-residue peptide modular units provide the ability to bind arbitrary RNA sequences, with high specificity and fidelity, by varying the sequence of the six-residue peptide modular units within the chains,
wherein the amino acids in positions 1 and 5 of each six-residue peptide modular unit provide the preferred affinity of the six residue peptide modular unit for the specific RNA base and the amino acid at position 2 of each six-residue peptide modular unit serves as a stacking unit between concatenated six residue peptide modular units;
concatenating selected ones of the six-residue peptide modular units into a chain of suitable composition and length for binding the RNA molecule; and
binding the RNA molecule to the chain of six or more six-residue peptide modular units.

16. The method of claim 15, wherein the six-residue peptide modular units have four canonic forms, with each canonic form having a preferred affinity for a different RNA base.

17. The method of claim 16, wherein the four canonic forms are characterized by the RNA base with which they have a preferred affinity, the two amino acids of the six-residue peptide modular unit that provide the preferred affinity for that base, and the amino acid of the six-residue peptide modular unit that serves as a stacking unit between concatenated six-residue peptide modular units.

18. The method of claim 17, the four canonic forms consisting of:
Form 1, which has a preferred affinity for RNA base Adenine, and has Cysteine at position 1, Tyrosine at position 2, and Glutamine at position 5;
Form 2, which has a preferred affinity for RNA base Uracil, and has Asparagine at position 1, Tyrosine at position 2, and Glutamine at position 5;
Form 3, which has a preferred affinity for RNA base Guanine, and has Serine at position 1, Tyrosine at position 2, and Glutamic Acid at position 5; and
Form 4, which has a preferred affinity for RNA base Cytosine, and has Serine at position 1, Tyrosine at position 2, and Arginine at position 5.

19. The method of claim 15, wherein the concatenated six-residue peptide modular units form 8-mers from the Pumilio Homology Domain.

20. The method of claim 18, wherein the concatenated six-residue peptide modular units form 8-mers from the Pumilio Homology Domain.

21. The method of claim 17, wherein the stacking unit at position 2 is Tyrosine or Arginine.

* * * * *